(12) United States Patent
Kuhlman et al.

(10) Patent No.: US 9,169,358 B2
(45) Date of Patent: Oct. 27, 2015

(54) POLYETHERIMIDES, METHODS OF MANUFACTURE, AND ARTICLES FORMED THEREFROM

(71) Applicant: SABIC GLOBAL TECHNOLOGIES B.V., Bergen Op Zoom (NL)

(72) Inventors: Matthew L Kuhlman, Evansville, IN (US); Gurulingamurthy M Haralur, Evansville, IN (US)

(73) Assignee: SABIC GLOBAL TECHNOLOGIES B.V. (NL)

( * ) Notice: Subject to any disclaimer, the term of this patent is extended or adjusted under 35 U.S.C. 154(b) by 0 days.

(21) Appl. No.: 14/541,543

(22) Filed: Nov. 14, 2014

(65) Prior Publication Data

US 2015/0073116 A1    Mar. 12, 2015

Related U.S. Application Data

(62) Division of application No. 13/283,951, filed on Oct. 28, 2011, now Pat. No. 8,907,042.

(51) Int. Cl.
| | |
|---|---|
| *C08G 73/10* | (2006.01) |
| *C07C 63/04* | (2006.01) |
| *C07C 63/22* | (2006.01) |
| *C07D 209/48* | (2006.01) |
| *C08G 65/40* | (2006.01) |
| *C08L 79/08* | (2006.01) |

(52) U.S. Cl.
CPC ............ *C08G 73/1003* (2013.01); *C07C 63/04* (2013.01); *C07C 63/22* (2013.01); *C07D 209/48* (2013.01); *C08G 65/40* (2013.01); *C08G 73/1042* (2013.01); *C08G 73/1046* (2013.01); *C08G 73/1053* (2013.01); *C08L 79/08* (2013.01); *Y10T 428/2942* (2015.01); *Y10T 428/3154* (2015.01)

(58) Field of Classification Search
CPC ..... C07C 63/04; C07C 63/22; C08G 73/1046
USPC ........... 521/180; 528/125, 126, 128, 170, 310
See application file for complete search history.

(56) References Cited

U.S. PATENT DOCUMENTS

| | | | |
|---|---|---|---|
| 3,847,867 | A | 11/1974 | Heath et al. |
| 4,217,438 | A | 8/1980 | Brunelle et al. |
| 4,988,544 | A | 1/1991 | Cella et al. |
| 5,229,482 | A | 7/1993 | Brunelle |

(Continued)

FOREIGN PATENT DOCUMENTS

| | | |
|---|---|---|
| EP | 2644641 A1 | 10/2013 |
| GB | 1392649 | 4/1975 |

(Continued)

OTHER PUBLICATIONS

International Search Report for International Application No. PCT/US2012/062183, Application Filing Date Oct. 26, 2012, Date of Mailing Feb. 28, 2013, 5 pages.

(Continued)

*Primary Examiner* — Gregory Listvoyb
(74) *Attorney, Agent, or Firm* — Cantor Colburn LLP; Diderico van Eyl

(57) ABSTRACT

A polyetherimide manufactured by reaction of an alkali metal salt of a dihydroxy aromatic compound of the formula

MO—Z—OM wherein M is an alkali metal salt and Z is an aromatic $C_{6-24}$ monocyclic or polycyclic moiety optionally substituted with 1 to 6 $C_{1-8}$ alkyl groups, 1 to 8 halogen atoms, or a combination thereof,
with a bis(halophthalimide) composition comprising, based on the weight of the bis(halophthalimide) composition,
from more than 45 to less than 75 weight percent of a 3,3'-bis(halophthalimide) of the formula

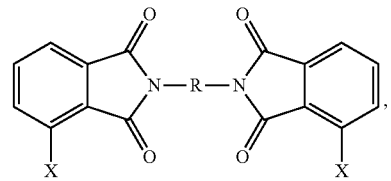

less than 10 weight percent of a 3,4'-bis(halophthalimide) of the formula

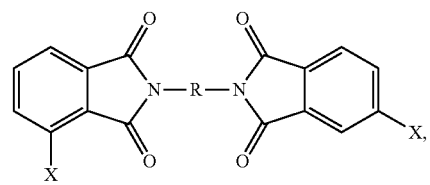

and
from more than 45 to less than 75 weight percent of a (4,4'-bis(halophthalimide) of the formula

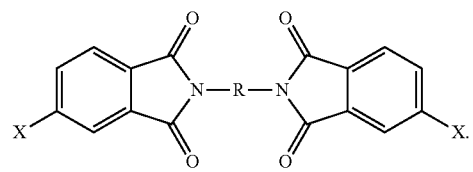

19 Claims, 2 Drawing Sheets

(56) References Cited

U.S. PATENT DOCUMENTS

| | | | |
|---|---|---|---|
| 5,830,974 | A | 11/1998 | Schmidhauser et al. |
| 5,908,915 | A | 6/1999 | Brunelle |
| 5,917,005 | A | 6/1999 | Brunelle et al. |
| 6,020,456 | A | 2/2000 | Brunelle et al. |
| 6,235,866 | B1 | 5/2001 | Khouri et al. |
| 6,849,706 | B1 | 2/2005 | Brunelle et al. |
| 6,906,168 | B2 | 6/2005 | Khouri et al. |
| 6,919,418 | B2 | 7/2005 | Khouri et al. |
| 7,481,959 | B2 | 1/2009 | Richards et al. |
| 7,714,095 | B2 | 5/2010 | Brunelle et al. |
| 8,357,773 | B1 | 1/2013 | Gallucci et al. |
| 2007/0043203 | A1 | 2/2007 | Ye et al. |
| 2013/0108852 | A1 | 5/2013 | Kuhlman et al. |
| 2015/0079376 | A1 | 3/2015 | Kuhlman |

FOREIGN PATENT DOCUMENTS

| | | |
|---|---|---|
| GB | 1485172 | 9/1977 |
| WO | 2009143440 A1 | 11/2009 |

OTHER PUBLICATIONS

White, D.M., et al., "Polyetherimides Via Nitro-Dispalcement Polymerization: Monomer Synthesis and 13C-NMR Analysis of Monomers and Polymers", Journal of Polymer Science: Polymer Chemistry Edition, vol. 19, 1635-1658 (1981).

Written Opinion for International Application No. PCT/US2012/062183, Application Filing Date Oct. 26, 2012, Date of Mailing Feb. 28, 2013, 13 pages.

Prior Art

POLYETHERIMIDES, METHODS OF MANUFACTURE, AND ARTICLES FORMED THEREFROM

CROSS REFERENCED TO RELATED APPLICATION

This application is a divisional application of U.S. patent application Ser. No. 13/283,951, filed on Oct. 28, 2011, which is incorporated by reference herein in its entirety.

BACKGROUND OF THE INVENTION

This disclosure relates to polyetherimides and compositions containing the polyetherimides, as well as their method of manufacture and articles formed from the polyetherimide compositions.

Polyetherimides ("PEIs") are amorphous, transparent, high performance polymers having a glass transition temperature ("Tg") of greater than 180° C. PEIs further have high strength, heat resistance, and modulus, and broad chemical resistance, and so are widely used in applications as diverse as automotive, telecommunication, aerospace, electrical/electronics, transportation, and healthcare.

Polyetherimides can be manufactured commercially by a "halo-displacement process." As shown in FIG. 1, a halogen-substituted anhydride is reacted with a diamine to form a bishalophthalimide. The bishalophthalimide is then reacted with a metal salt of a dihydroxy compound. Despite extensive investigation into the manufacture of polyetherimides produced using the halo-displacement process, there nonetheless remains a need for further improvement. For example, some polyetherimides are currently manufactured using a 95:5 ratio of the 4-isomer to the 3-isomer of the halophthalic anhydride, which yields a product having excellent ductility. Increasing the relative ratio of the 3-isomer can enhance flow and Tg of the polyetherimides, but ratios of 90:10 or below results in a dramatic loss of ductility.

There accordingly remains a need in the art for polyetherimides and methods for the manufacture of polyetherimides having improved properties, in particular polyetherimides having improved Tg and flow, without significantly adversely affecting ductility. It would be a further advantage if such improvements were obtained without significantly adversely affecting other desirable properties of the polyetherimides, for example one or more of heat deflection temperature, Vicat, and high tensile strength at yield.

SUMMARY OF THE INVENTION

In an embodiment, a polymer composition comprises a polyetherimide of the formula

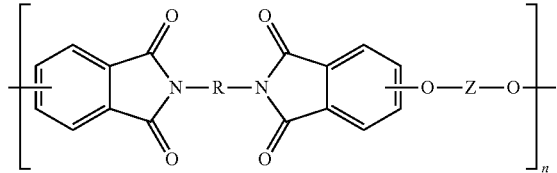

wherein n is greater than 1, each R is the same or different, and is wherein R is selected from an aromatic hydrocarbon group having 6 to 30 carbon atoms, a halogenated derivative thereof, a straight or branched chain alkylene group having 2 to 10 carbon atoms, a cycloalkylene group having 3 to 20 carbon atoms, or a divalent group of the formula

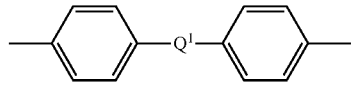

wherein $Q^1$ is selected from —O—, —S—, —C(O)—, —SO$_2$—, —SO—, —C$_y$H$_{2y}$— wherein y is 1 to 5, and a halogenated derivative thereof, each Z is the same or different and is an aromatic C$_{6-24}$ monocyclic or polycyclic moiety optionally substituted with 1 to 6 C$_{1-8}$ alkyl groups, 1 to 8 halogen atoms, or a combination thereof, and the divalent bonds between the —O—Z—O— group and the phenyl substituents are in the 3,3', 3,4', 4,3', and 4,4' positions; the divalent bonds of the —O—Z—O— group being made from a bis(halophthalimide) composition comprising, based on the weight of the bis(halophthalimide) composition, from more than 45 to less than 75 weight percent of a 3,3'-bis(halophthalimide) of the formula

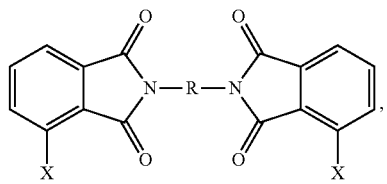

less than 10 weight percent of a 3,4'-bis(halophthalimide) of the formula

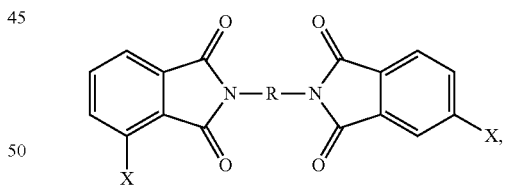

and from more than 45 to less than 75 weight percent of a (4,4'-bis(halophthalimide) of the formula

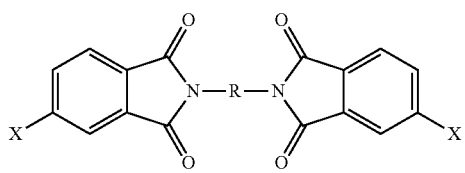

wherein X is halogen and R is as defined above.

In another embodiment, a polymer composition comprises a polyetherimide of the formula

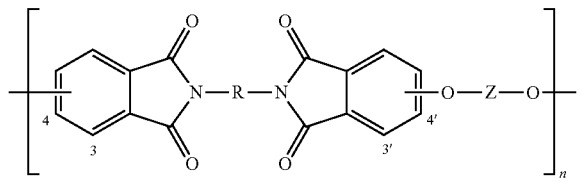

wherein n is greater than 1, each R is the same or different, and is wherein R is selected from an aromatic hydrocarbon group having 6 to 30 carbon atoms, a halogenated derivative thereof, a straight or branched chain alkylene group having 2 to 10 carbon atoms, a cycloalkylene group having 3 to 20 carbon atoms, or a divalent group of the formula

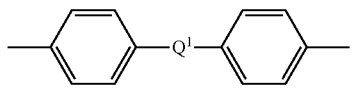

wherein $Q^1$ is selected from —O—, —S—, —C(O)—, —SO$_2$—, —SO—, —C$_y$H$_{2y}$— wherein y is 1 to 5, and a halogenated derivative thereof, each Z is the same or different and is an aromatic C$_{6-24}$ monocyclic or polycyclic moiety optionally substituted with 1 to 6 C$_{1-8}$ alkyl groups, 1 to 8 halogen atoms, or a combination thereof, and the divalent bonds between the —O—Z—O— group and the phenyl substituents are in the 3,3', 3,4', 4,3', and 4,4' positions; the divalent bonds of the —O—Z—O— group being made from a bis(halophthalimide) composition comprising, based on the weight of the bis(halophthalimide) composition, from more than 45 to less than 75 weight percent of a 3,3'-bis(halophthalimide) of the formula

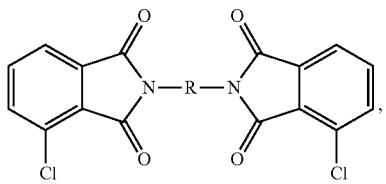

less than 10 weight percent of a 3,4'-bis(halophthalimide) of the formula

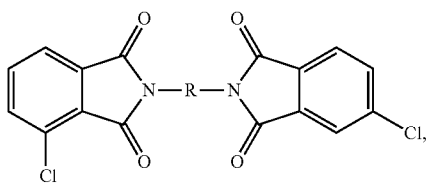

and from more than 45 to less than 75 weight percent of a (4,4'-bis(halophthalimide) of the formula

wherein R is as defined above.

In still another embodiment, a polyetherimide composition comprises a polyetherimide manufactured by reaction of an alkali metal salt of a dihydroxy aromatic compound of the formula

MO—Z—OM wherein M is an alkali metal salt and Z is an aromatic C$_{6-24}$ monocyclic or polycyclic moiety optionally substituted with 1 to 6 C$_{1-8}$ alkyl groups, 1 to 8 halogen atoms, or a combination thereof, with a bis(halophthalimide) composition comprising, based on the weight of the bis(halophthalimide) composition, from more than 45 to less than 75 weight percent of a 3,3'-bis(halophthalimide) of the formula

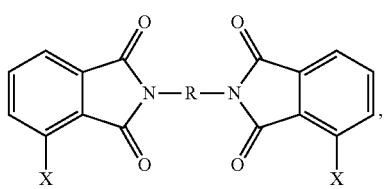

less than 10 weight percent of a 3,4'-bis(halophthalimide) of the formula

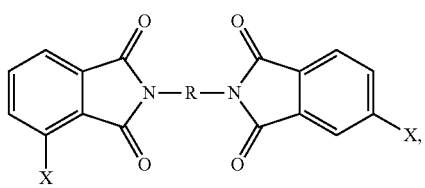

and from more than 45 to less than 75 weight percent of a (4,4'-bis(halophthalimide) of the formula

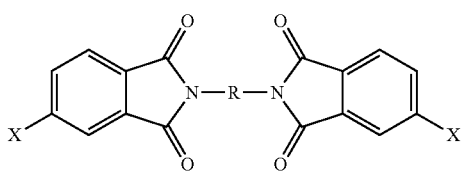

wherein R is selected from an aromatic hydrocarbon group having 6 to 30 carbon atoms, a halogenated derivative thereof, a straight or branched chain alkylene group having 2 to 10 carbon atoms, a cycloalkylene group having 3 to 20 carbon atoms, or a divalent group of the formula

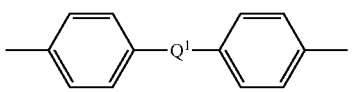

wherein $Q^1$ is selected from —O—, —S—, —C(O)—, —SO$_2$—, —SO—, —C$_y$H$_{2y}$— wherein y is 1 to 5, and a halogenated derivative thereof, further wherein
the polyetherimide is of the formula

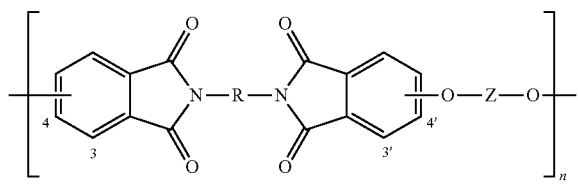

wherein n is greater than 1, each R is the same or different, each Z is the same or different, and are as defined above, and the divalent bonds between the —O—Z—O— group and the phenyl substituents are in the 3,3', 3,4', 4,3', and 4,4' positions.

Also disclosed is a polyetherimide composition comprising a polyetherimide manufactured by reaction of an alkali metal salt of a dihydroxy aromatic compound of the formula

MO—Z—OM wherein M is an alkali metal salt and Z is an aromatic C$_{6-24}$ monocyclic or polycyclic moiety optionally substituted with 1 to 6 C1-8 alkyl groups, 1 to 8 halogen atoms, or a combination thereof, with a bis(chlorophthalimide) composition comprising, based on the weight of the bis(chlorophthalimide) composition, from more than 45 to less than 75 weight percent of a 3,3'-bis(chlorophthalimide) of the formula

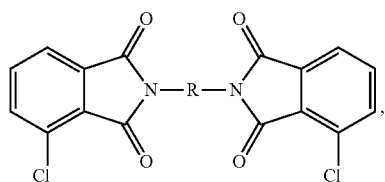

less than 10 weight percent of a 3,4'-bis(chlorophthalimide) of the formula

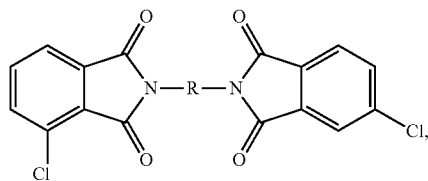

and
from more than 45 to less than 75 weight percent of a 4,4'-bis(chlorophthalimide) of the formula

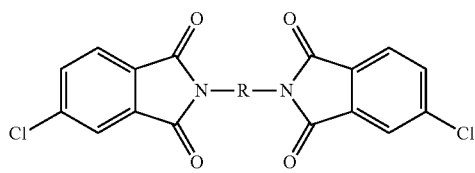

wherein R is selected from an aromatic hydrocarbon group having 6 to 30 carbon atoms, a halogenated derivative thereof, a straight or branched chain alkylene group having 2 to 10 carbon atoms, a cycloalkylene group having 3 to 20 carbon atoms, or a divalent group of the formula

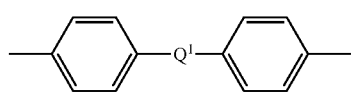

wherein $Q^1$ is selected from —O—, —S—, —C(O)—, —SO$_2$—, —SO—, —C$_y$H$_{2y}$— wherein y is 1 to 5, and a halogenated derivative thereof, further wherein the polyetherimide is of the formula

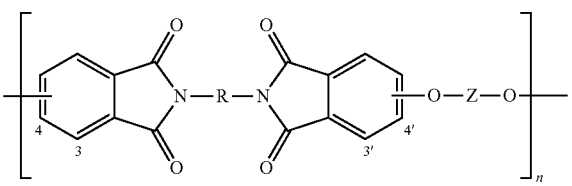

wherein n is greater than 1, each R is independently the same or different, each Z is independently the same or different, and are as defined above, and the divalent bonds between the —O—Z—O— group and the phenyl substituents are in the 3,3', 3,4', 4,3', and 4,4' positions.

A method of manufacturing the above polyetherimides includes reacting, in the presence of a catalytically active amount of a phase transfer catalyst, the alkali metal salt of the dihydroxy aromatic compound with the bis(halophthalimide) composition to form the polyetherimides.

A method for the manufacture of a bis(halophthalimide) composition from a combination of a 4-halophthalic anhydride isomer of the formula

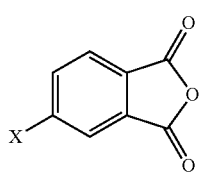

and a 3-halophthalic anhydride isomer of the formula

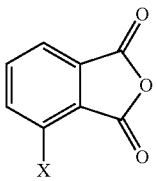

wherein X is a halogen, in a ratio of the 4-halophthalic anhydride to 3-halophthalic anhydride of 90:10 to 10:90, the method comprising reacting at least 80 mole percent of the total amount of one isomer with a diamine of the formula

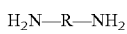

wherein R is selected from an aromatic hydrocarbon group having 6 to 30 carbon atoms, a halogenated derivative thereof, a straight or branched chain alkylene group having 2 to 10 carbon atoms, a cycloalkylene group having 3 to 20 carbon atoms, or a divalent group of the formula

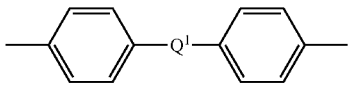

wherein $Q^1$ is selected from —O—, —S—, —C(O)—, —SO$_2$—, —SO—, —C$_y$H$_{2y}$— wherein y is 1 to 5, and a halogenated derivative thereof, to form a bis(halophthalimide) to form a reaction mixture comprising a bis(halophthalimide); adding at least 80 mole percent of the total amount of the other isomer and another portion of the diamine to the reaction mixture, to form a bis(halophthalimide) composition comprising, based on the total weight of the composition, from more than 45 to less than 75 weight percent of a 3,3'-bis(halophthalimide) of the formula

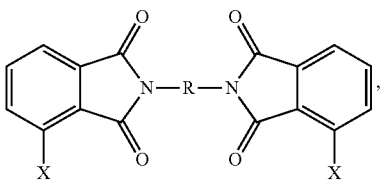

less than 10 weight percent of a 4,3'-bis(halophthalimide) of the formula

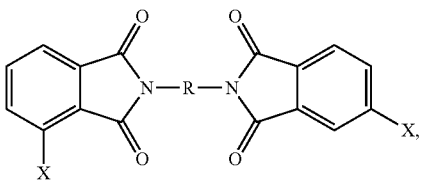

and from more than 45 to less than 75 weight percent of a (4,4'-bis(halophthalimide) of the formula

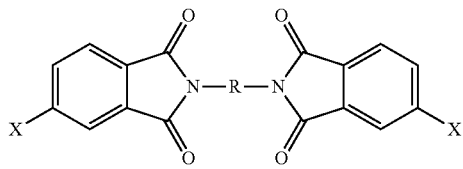

wherein X and R are as defined above.

In another embodiment, a polyetherimide is of the formula

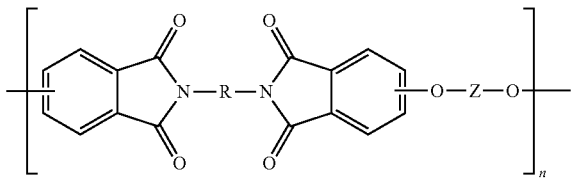

wherein based on the total weight percent of the —O—Z—O— groups in the polyetherimide, from more than more than 45 to less than 75 weight percent the divalent bonds of the —O—Z—O— groups are in the 3,3' position, less than 10 weight percent of the —O—Z—O— groups are in the 3,4', and 4',3 positions, and from more than 45 to less than 75 weight percent of the —O—Z—O— groups are 4,4' position; n is greater than 1; each R is independently an aromatic hydrocarbon group having 6 to 30 carbon atoms, a halogenated derivative thereof, a straight or branched chain alkylene group having 2 to 10 carbon atoms, a cycloalkylene group having 3 to 20 carbon atoms, or a divalent group of the formula

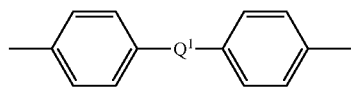

wherein $Q^1$ is selected from —O—, —S—, —C(O)—, —SO$_2$—, —SO—, and —C$_y$H$_{2y}$— wherein y is 1 to 5 and a halogenated derivative thereof; and Z is an aromatic $C_{6-24}$ monocyclic or polycyclic moiety optionally substituted with 1 to 6 C1-8 alkyl groups, 1 to 8 halogen atoms, or a combination thereof.

Compositions comprising the above polyetherimides are disclosed.

A method of manufacture of the above compositions includes melt blending the compositions of the aforementioned composition.

Articles comprising the above compositions are also disclosed. In an embodiment, the article is selected from a reflector, an optical lens, a fiber optic connector, and an adhesive, specifically an adhesive for adhering a metal to a fluoropolymer such as poly(tetrafluoroethylene). In another embodiment, an article comprises (i) a polytetrafluoroethylene substrate having a first surface, (ii) a metal substrate having a second surface, and (iii) the polymer composition of claim 1, situated between the polytetrafluoroethylene substrate and the metal substrate.

A method of forming the above articles includes shaping, extruding, blow molding, or injection molding the above compositions to form the article.

The invention is further illustrated by the Drawings, Detailed Description, and Examples.

DETAILED DESCRIPTION OF THE INVENTION

Figure 1:
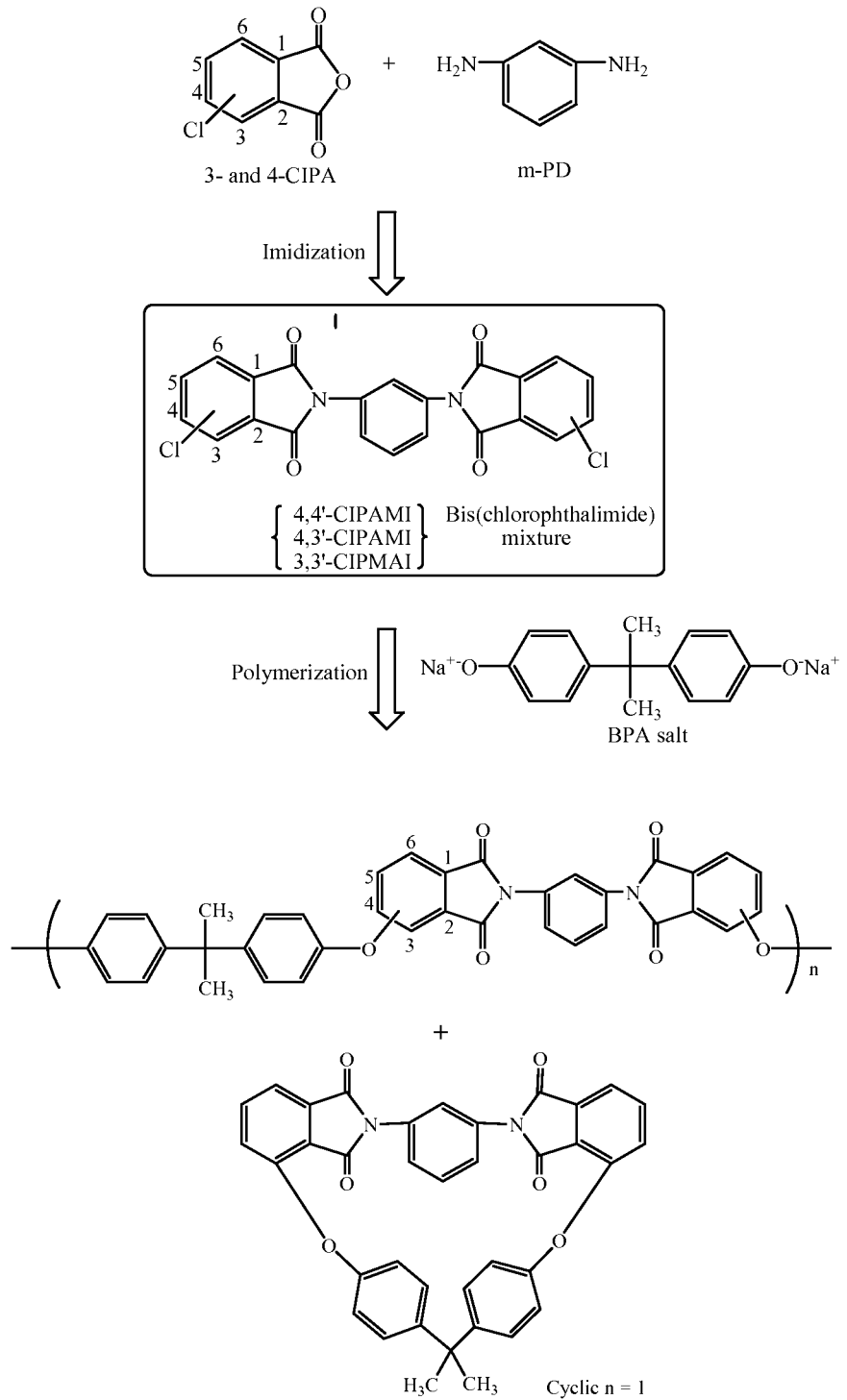
FIG. 1 shows a reaction scheme illustrating a chloro-displacement process for the manufacture of the polyetherimides.

The present inventors have discovered that precise control of the bis(halophthalimide) regioisomers used in the preparation of polyetherimides by the halo-displacement process provides polyetherimides having very good ductility, as well as improved flow and Tg. Furthermore, the polyetherimides can have improved chemical and physical properties, including one or more of heat deflection temperature, and Vicat, as well as improved high tensile strength at yield.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed in this patent application. Because these ranges are continuous, they include every value between the minimum and maximum values. Unless expressly indicated otherwise, the various numerical ranges specified in this application are approximations. The endpoints of all ranges directed to the same composition or property are inclusive of the endpoint and independently combinable.

All molecular weights in this application refer to weight average molecular weights unless indicated otherwise. All such mentioned molecular weights are expressed in amu.

The terms "a" and "an" do not denote a limitation of quantity, but rather denote the presence of at least one of the referenced item. As used herein, "combination thereof" is inclusive of one or more of the recited elements, optionally together with a like element not recited. Reference throughout the specification to "one embodiment," "another embodiment," "an embodiment," "some embodiments," and so forth, means that a particular element (e.g., feature, structure, property, and/or characteristic) described in connection with the embodiment is included in at least one embodiment described herein, and can or can not be present in other embodiments. In addition, it is to be understood that the described element(s) can be combined in any suitable manner in the various embodiments.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

The term "alkyl" includes both $C_{1-30}$ branched and straight chain, unsaturated aliphatic hydrocarbon groups having the specified number of carbon atoms, e.g., methyl, ethyl, n-propyl, i-propyl, n-butyl, s-butyl, t-butyl, n-pentyl, s-pentyl, n- and s-hexyl, n- and s-heptyl, and, n- and s-octyl. "Alkylene" means a straight or branched chain, saturated, divalent aliphatic hydrocarbon group (e.g., methylene (—$CH_2$—) or, propylene (—$(CH_2)_3$—)). "Alkoxy" means an alkyl group that is linked via an oxygen (i.e., alkyl-O—), for example methoxy, ethoxy, and sec-butyloxy groups.

"Alkenyl" means a straight or branched chain, monovalent hydrocarbon group having at least one carbon-carbon double bond (e.g., ethenyl (—HC=$CH_2$)).

"Cycloalkylene" means a divalent cyclic alkylene group, —$C_nH_{2n-x}$, wherein x represents the number of hydrogens replaced by cyclization(s). "Cycloalkenyl" means a monovalent group having one or more rings and one or more carbon-carbon double bond in the ring, wherein all ring members are carbon (e.g., cyclopentyl and cyclohexyl).

The term "aryl" means an aromatic moiety containing the specified number of carbon atoms, such as to phenyl, tropone, indanyl, or naphthyl.

The prefix "halo" means a group or compound including one more of a fluoro, chloro, bromo, iodo, and astatino substituent. A combination of different halo groups (e.g., bromo and fluoro) can be present. In a embodiment only chloro groups are present.

The prefix "hetero" means that the compound or group includes at least one ring that is a heteroatom (e.g., 1, 2, or 3 heteroatom(s)), wherein the heteroatom(s) is each independently N, O, S, Si, or P.

"Substituted" means that the compound or group is substituted with at least one (e.g., 1, 2, 3, or 4) substituent independently selected from a $C_{1-9}$ alkoxy, a $C_{1-9}$ haloalkoxy, a nitro (—$NO_2$), a cyano (—CN), a C1-6 alkyl sulfonyl (—S(=O)$_2$-alkyl), a $C_{6-12}$ aryl sulfonyl (—S(=O)$_2$-aryl)a thiol (—SH), a thiocyano (—SCN), a tosyl ($CH_3C_6H_4SO_2$—), a C3 to C12 cycloalkyl, a C2 to C12 alkenyl, a C5 to C12 cycloalkenyl, a C6 to C12 aryl, a C7 to C13 arylalkylene, a C4 to C12 heterocycloalkyl, and a C3 to C12 heteroaryl instead of hydrogen, provided that the substituted atom's normal valence is not exceeded.

All ASTM tests are based on the 2003 edition of the Annual Book of ASTM Standards unless otherwise indicated.

The polyetherimides are of formula (1)

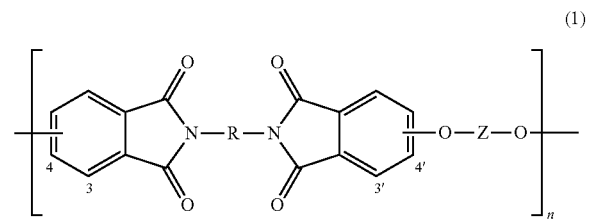

(1)

wherein n is greater than 1, for example 10 to 1,000 or more, or more specifically 10 to 500.

The group R in formula (1) is a substituted or unsubstituted divalent organic group, such as a $C_{6-30}$ or $C_{6-20}$ aromatic hydrocarbon group or a halogenated derivative thereof, a straight or branched chain $C_{2-20}$ alkylene group or a halogenated derivative thereof, a $C_{3-8}$ cycloalkylene group or a halogenated derivative thereof, or a divalent group of formula (2)

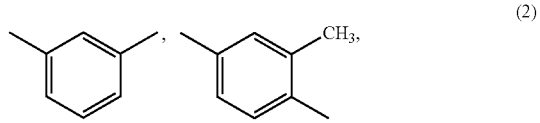

(2)

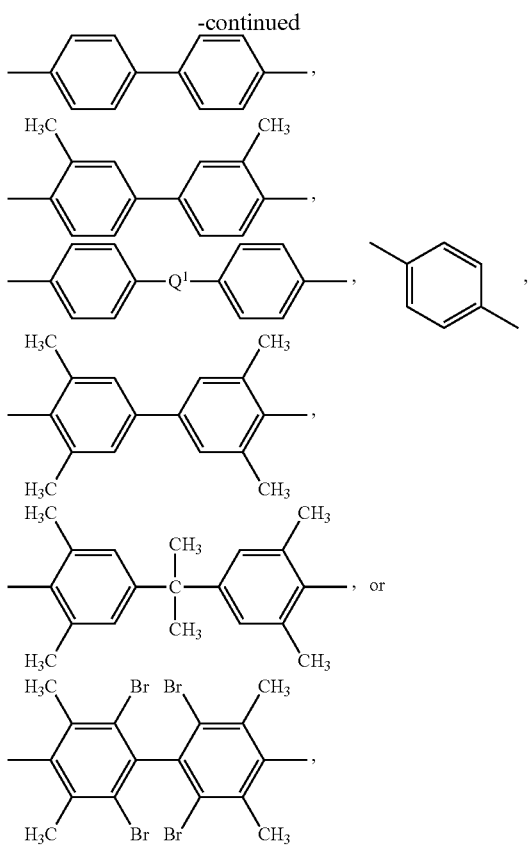

wherein $Q^1$ is —O, S, C(O)—, —SO$_2$—, —SO—, and —C$_y$H$_{2y}$— and a halogenated derivative thereof (which includes perfluoroalkylene groups) wherein y is an integer from 1 to 5. In a specific embodiment R is a m-phenylene or p-phenylene.

The group Z in formula (1) is also a substituted or unsubstituted divalent organic group, and can be an aromatic C$_{6-24}$ monocyclic or polycyclic moiety optionally substituted with 1 to 6 C$_{1-8}$ alkyl groups, 1 to 8 halogen atoms, or a combination thereof, provided that the valence of Z is not exceeded. Exemplary groups Z include groups derived from a dihydroxy compound of formula (3):

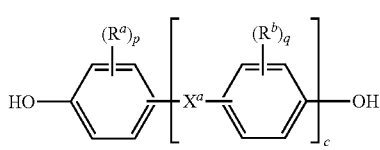

(3)

wherein R$a^a$ and R$^b$ each represent a halogen atom or a monovalent hydrocarbon group and can be the same or different; p and q are each independently integers of 0 to 4; c is 0 to 4; and X$^a$ is a bridging group connecting the hydroxy-substituted aromatic groups, where the bridging group and the hydroxy substituent of each C$_6$ arylene group are disposed ortho, meta, or para (specifically para) to each other on the C$_6$ arylene group. The bridging group X$^a$ can be a single bond, —O—, —S—, —S(O)—, —S(O)$_2$—, —C(O)—, or a C$_{1-18}$ organic group. The C$_{1-18}$ organic bridging group can be cyclic or acyclic, aromatic or non-aromatic, and can further comprise heteroatoms such as halogens, oxygen, nitrogen, sulfur, silicon, or phosphorous. The C$_{1-18}$ organic group can be disposed such that the C$_6$ arylene groups connected thereto are each connected to a common alkylidene carbon or to different carbons of the C$_{1-18}$ organic bridging group. A specific example of a group Z is a divalent group of formulas (3a)

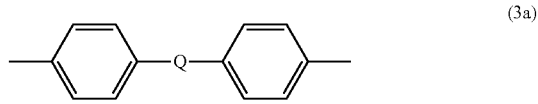

(3a)

wherein Q is —O—, —S—, —C(O)—, —SO$_2$—, —SO—, and —C$_y$H$_{2y}$— and a halogenated derivative thereof (including a perfluoroalkylene group) wherein y is an integer from 1 to 5. In a specific embodiment Z is derived from bisphenol A wherein Q is 2,2-isopropylidene.

In another specific embodiment, the polyetherimide comprises more than 1, specifically 10 to 1,000, or more specifically, 10 to 500 structural units, of formula (1) wherein R is a divalent group of formula (2) wherein $Q^1$ is —C$_y$H$_{2y}$— wherein y is an integer from 1 to 5 or a halogenated derivative thereof, and Z is a group of formula (3). In a specific embodiment, R is m-phenylene, p-arylene diphenylsulfone, or a combination thereof, and Z is 2,2-(4-phenylene)isopropylidene. For example, a polyetherimide sulfone comprises structural units of formula (1) wherein at least 50 mole % of the R groups are of formula (2) wherein $Q^1$ is —SO$_2$— and the remaining R groups are independently p-phenylene or m-phenylene or a combination comprising at least one of the foregoing; and Z is 2,2-(4-phenylene)isopropylidene.

The polyetherimide can be a copolymer, and combinations of polyetherimides can be used. In an embodiment, the polyetherimide optionally comprises additional structural imide units, for example imide units of formula (4)

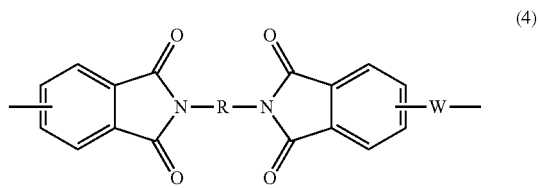

(4)

wherein R is as described in formula (1) and W is a linker of formulas (5)

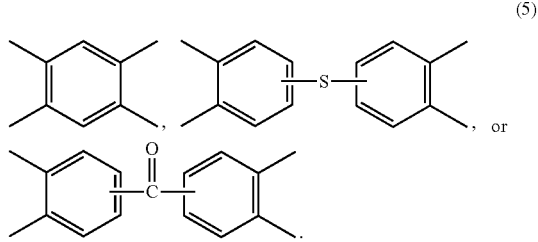

(5)

These additional structural imide units can be present in amounts ranging from 0 to 10 mole % of the total number of units, specifically 0 to 5 mole %, more specifically 0 to 2 mole %. In one embodiment no additional imide units are present in the polyetherimide.

The polyetherimides are prepared by the so-called "halo-displacement" or "chloro-displacement" method. In this method, a halophthalic anhydride of formula (6)

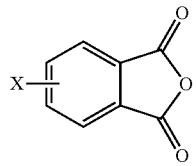

(6)

wherein X is a halogen, is condensed with an organic diamine of the formula (7)

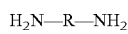

(7)

wherein R is as described in formula (1), to form a bis(halophthalimide) of formula (8).

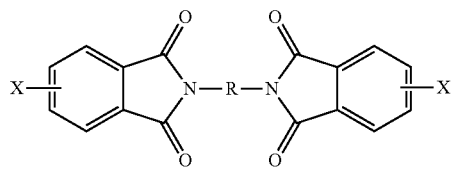

(8)

In an embodiment, X is a halogen, specifically fluoro, chloro, bromo, or iodo, more specifically chloro. A combination of different halogens can be used.

Illustrative examples of amine compounds of formula (7) include ethylenediamine, propylenediamine, trimethylenediamine, diethylenetriamine, triethylenetetramine, hexamethylenediamine, heptamethylenediamine, octamethylenediamine, nonamethylenediamine, decamethylenediamine, 1,12-dodecanediamine, 1,18-octadecanediamine, 3-methylheptamethylenediamine, 4,4-dimethylheptamethylenediamine, 4-methylnonamethylenediamine, 5-methylnonamethylenediamine, 2,5-dimethylhexamethylenediamine, 2,5-dimethylheptamethylenediamine, 2,2-dimethylpropylenediamine, N-methyl-bis(3-aminopropyl)amine, 3-methoxyhexamethylenediamine, 1,2-bis(3-aminopropoxy) ethane, bis(3-aminopropyl) sulfide, 1,4-cyclohexanediamine, bis-(4-aminocyclohexyl) methane, m-phenylenediamine, p-phenylenediamine, 2,4-diaminotoluene, 2,6-diaminotoluene, m-xylylenediamine, p-xylylenediamine, 2-methyl-4,6-diethyl-1,3-phenylene-diamine, 5-methyl-4,6-diethyl-1,3-phenylene-diamine, benzidine, 3,3'-dimethylbenzidine, 3,3'-dimethoxybenzidine, 1,5-diaminonaphthalene, bis(4-aminophenyl) methane, bis(2-chloro-4-amino-3,5-diethylphenyl) methane, bis(4-aminophenyl) propane, 2,4-bis(b-amino-t-butyl) toluene, bis(p-b-amino-t-butylphenyl) ether, bis(p-b-methyl-o-aminophenyl)benzene, bis(p-b-methyl-o-aminopentyl)benzene, 1,3-diamino-4-isopropylbenzene, bis(4-aminophenyl) ether and 1,3-bis(3-aminopropyl)tetramethyldisiloxane. Combinations of these amines can be used. Illustrative examples of amine compounds of formula (7) containing sulfone groups include diamino diphenyl sulfone (DDS) and bis(aminophenoxy phenyl) sulfones (BAPS). Combinations comprising any of the foregoing amines can be used.

In a specific embodiment diamine (7) is a meta-phenylene diamine (7a) or a para-phenylene diamine (7b)

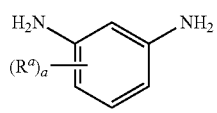

(7a)

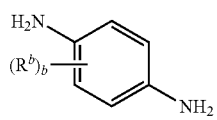

(7b)

wherein $R^1$ and $R^2$ are each independently a halogen atom, nitro, cyano, $C_2$-$C_{20}$ aliphatic group, $C_2$-$C_{40}$ aromatic group, and a and b are each independently 0 to 4. Specific examples include meta-phenylenediamine (mDA), para-phenylenediamine (pDA), 2,4-diaminotoluene, 2,6-diaminotoluene, 2-methyl-4,6-diethyl-1,3-phenylenediamine, 5-methyl-4,6-diethyl-1,3-phenylenediamine, or 1,3-diamino-4-isopropylbenzene. Combinations comprising any of the foregoing amines can be used.

Condensation of halophthalic anhydride (6) and amine (7) (imidization) can be conducted in the absence or presence of a catalyst. Exemplary phase transfer catalysts for imidization include sodium phenyl phosphinate (SPP), acetic acid, hexaethylguanidinium, benzoic acid, phthalic acid, or substituted derivatives thereof. In an embodiment, sodium phenyl phosphinate is used as the imidization catalyst. The catalyst, if used, is present in an amount effective to accelerate the reaction, for example about 0.1-0.3 wt. % based on the weight of diamine.

The reaction is generally conducted in the presence of a relatively non-polar solvent, preferably with a boiling point above about 100° C., specifically above about 150° C., for example o-dichlorobenzene, dichlorotoluene, 1,2,4-trichlorobenzene, diphenyl sulfone, a monoalkoxybenzene such as anisole, veratrole, diphenylether, or phenetole. Ortho-dichlorobenzene and anisole can be particularly mentioned.

The bis(halophthalimide)s (8) are generally prepared at least 110° C., specifically 150° to 275° C., more specifically 175 to 225° C. At temperatures below 110° C., reaction rates can be too slow for economical operation. Atmospheric or super-atmospheric pressures can be used, for example up to 5 atmospheres, to facilitate the use of high temperatures without causing solvent to be lost by evaporation.

The solvent, diamine (7), and halophthalic anhydride (6) can be combined in amounts such that the total solids content during the reaction to form bis(halophthalimide) (8) does not exceed about 25 wt. %, or about 17 wt. %. "Total solids content" expresses the proportion of the reactants as a percentage of the total weight comprising liquids present in the reaction at any given time.

A molar ratio of halophthalic anhydride (6) to diamine (7) of 1.98:1 to 2.04:1, specifically 2:1 is used. While other ratios can be employed, a slight excess of anhydride or diamine can be desirable. A proper stoichiometric balance between halophthalic anhydride (6) and diamine (7) is maintained to prevent undesirable by-products that can limit the molecular weight of the polymer, and/or result in polymers with amine end groups. Accordingly, in an embodiment, imidization proceeds adding diamine (7) to a mixture of halophthalic anhydride (6) and solvent to form a reaction mixture having a targeted initial molar ratio of halophthalic anhydride to diamine; heating the reaction mixture to a temperature of at least 100° C. (optionally in the presence of an imidization catalyst); analyzing the molar ratio of the heated reaction mixture to determine the actual initial molar ratio of halophthalic anhydride (6) to diamine (7); and, if necessary, adding halophthalic anhydride (6) or diamine (7) to the analyzed reaction mixture to adjust the molar ratio of halophthalic anhydride (6) to diamine (7) to 2.01 to 2.3.

After imidization, the halogen group X of bis(halophthalimide) (8)

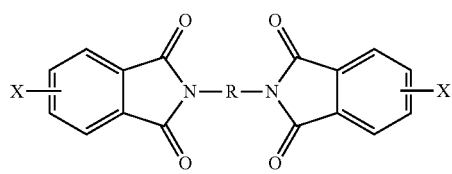

(8)

is displaced by reaction with an alkali metal salt of a dihydroxy aromatic compound of formula (9)

MO—Z—OM      (9)

wherein M is an alkali metal and Z is as described in formula (1), to provide the polyetherimide of formula (1)

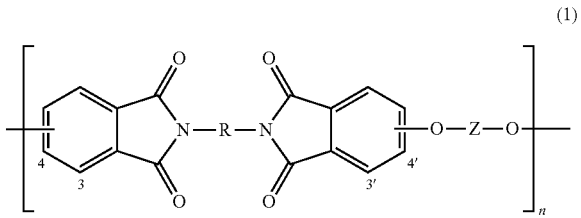

(1)

wherein n, R, and Z are as defined above.

The alkali metal M can be any alkali metal, and is typically potassium or sodium. The alkali metal salt can be obtained by reaction of the metal with an aromatic $C_{6-24}$ monocyclic or polycyclic dihydroxy compound optionally substituted with 1 to 6 $C_{1-8}$ alkyl groups, 1 to 8 halogen atoms, or a combination thereof, for example a compound of formula (3), more specifically a dihydroxy compound corresponding to one of the groups of formulas (3a), and still more specifically a bisphenol compound of formula (10):

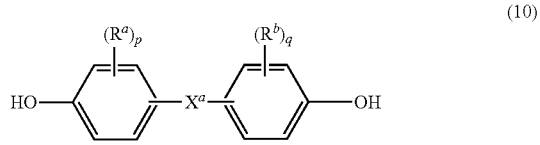

(10)

wherein $R^a$, $R^b$, and $X^a$ are as described in formula (3). For example, 2,2-bis(4-hydroxyphenyl) propane ("bisphenol A" or "BPA") can be used.

Polymerization by reaction of bis(halophthalimide) (8) with alkali metal salt (9) can be conducted in the presence or absence of phase transfer catalyst that is substantially stable under the reaction conditions used, in particular temperature. Exemplary phase transfer catalysts for polymerization include hexaalkylguanidinium and α,ω-bis(pentaalkylguanidinium)alkane salts. Both types of salts can be referred to herein as "guanidinium salts."

Polymerization is generally conducted in the presence of a relatively non-polar solvent, preferably with a boiling point above about 100° C., specifically above about 150° C., for example o-dichlorobenzene, dichlorotoluene, 1,2,4-trichlorobenzene, diphenyl sulfone, a monoalkoxybenzene such as anisole, veratrole, diphenylether, or phenetole. Ortho-dichlorobenzene and anisole can be particularly mentioned. Alternatively, a polar aprotic solvent can be used, illustrative examples of which include dimethylformamide (DMF), dimethylacetamide (DMAc), dimethylsulfoxide (DMSO), and N-methylpyrolidinone (NMP). A combination comprising at least one of the foregoing solvents can be used.

Polymerization can be conducted at a temperature of at least 110° C., specifically 150° to 275° C., more specifically 175 to 225° C. At temperatures below 110° C., reaction rates can be too slow for economical operation. Atmospheric or super-atmospheric pressures can be used, for example up to 5 atmospheres, to facilitate the use of high temperatures without causing solvent to be lost by evaporation.

In an embodiment, alkali metal salt (9) is added to the organic solvent and the water is removed from the mixture, for example as its azeotrope. The bis(halophthalimide) (8) is then added and water removed from the mixture, for example as its azeotrope, followed by addition of a catalyst in a pre-dried solution in organic solvent. Water removal from the system can be accomplished in either batch, semi-continuous or continuous processes using means known in the art such as a distillation column in conjunction with one or more reactors. In an embodiment, a mixture of water and non-polar organic liquid distilling from a reactor is sent to a distillation column where water is taken off overhead and solvent is recycled back into the reactor at a rate to maintain or increase the desired solids concentration. Other methods for water removal include passing the condensed distillate through a drying bed for chemical or physical adsorption of water.

The molar ratio of the bis(halophthalimide) (8) to the alkali metal salt (9) can be about 1.0:0.9 to 0.9:1.0. A solids content of the bis(halophthalimide) (8) in the polymerization can be 15 to 40 wt. %, based on the total weight of the polymerization mixture.

Thus, a method for the manufacture of the polyetherimides from the bis(halophthalimide) composition comprises reacting, in the presence of a catalytically active amount of a phase transfer catalyst, the alkali metal salt (9) with a bis(halophthalimide) (8). It has been discovered by the inventors hereof that desirable properties of the polyetherimide can be obtained by careful selection of the regioisomers of the bis(halophthalimide)s (8) used to manufacture the polyetherimides. In particular, the bis(halophthalimide)s (8) can be formed from the 3-halophthalic anhydride (6a) and/or the 4-halophthalic anhydride (6b)

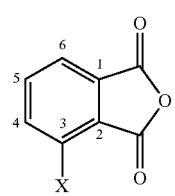

(6a)

-continued

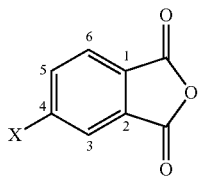
(6b)

to provide the 3,3'-bis(halophthalimide) (8a), the 3,4'-bis(halophthalimide) (8b), and/or the 4,4'-bis(halophthalimide) (8c).

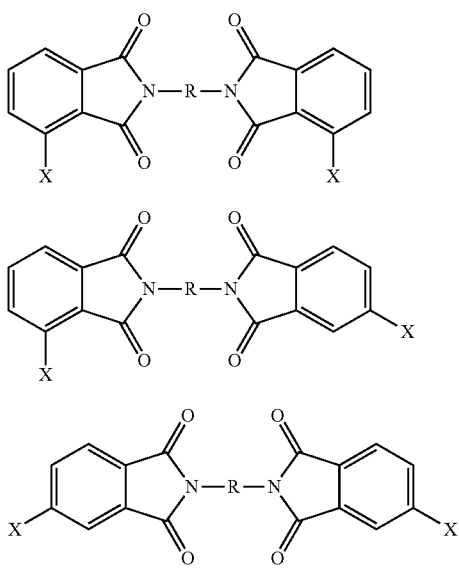

As can be seen from formula (8b), when R is symmetrical (e.g., a 1,3-phenylene or 1,4-phenylene) the 3,4'- and 3,4' isomers are the same, but when R is not symmetrical (e.g., 1-methyl-2,3-phenylene) the 3,4' and 4,3' regioisomers are not the same. Reference to the 3,4' isomer herein and in the claims specifically includes the 4,3' isomer irrespective of whether R is symmetrical. In a specific embodiment, a combination of 3-chlorophthalic anhydride (3-C1PA), 4-chlorophthalic anhydride (4-C1PA) and a diamine (7) (e.g., meta-phenylene diamine as shown in FIG. 1) are reacted to produce the bis(chlorophthalimide) (C1PAMI) composition as a mixture of the 3,3'-bis(chlorophthalimide) (3,3'-C1PAMI) (in FIG. 1, 1,3-bis[N-(3-chlorophthalimido)]benzene), the 3,4'-bis(chloropthalimide) (3,4'-C1PAMI) (in FIG. 1, 1,3-bis[N-(3-chlorophthalimido, 4-chlorophthalimido)]benzene), and the 4,4'-bis(chloropthalimide) (4,4'-C1PAMI) (in FIG. 1, 1,3-bis[N-(4-chlorophthalimido)]benzene).

Figure 2:
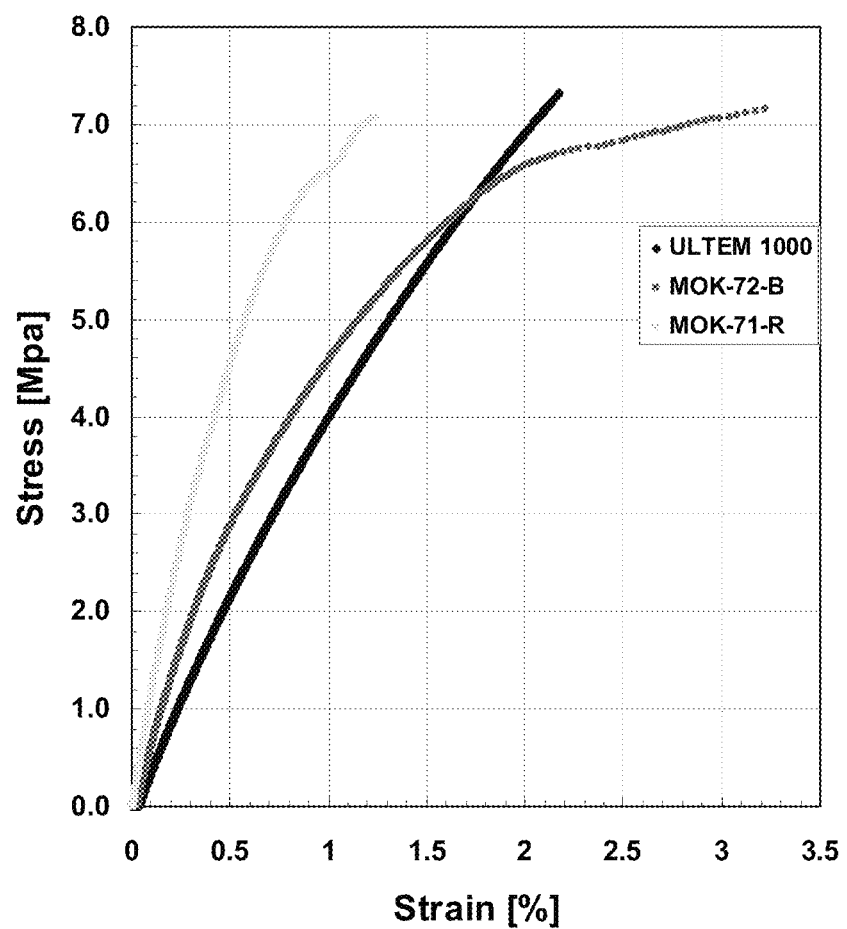
FIG. 2 is a graph illustrating a stress/Strain analysis for polymers made from sequential and one-pot C1PAMI synthesis.

Without being bound by theory, it is believed that the polyetherimides of our invention exhibit lower modulus and enhanced ductility because the amount of the 3,4'-bis(halophthalimide) (8b) (e.g., the 3,4'-C1PAMI isomer) is reduced. When the 3,4'-C1PAMI isomer is reduced, computer modeling experiments have shown that a polyetherimide produced from 4,4'-C1PAMI and 3'3'-C1PAMI (with relatively small amounts of 3,4'-C1PAMI isomer, the resulting polyetherimide has polymer chains that more linear than when the polyetherimide is made higher amounts of 3,4'-C1PAMI isomers. Computer modeling experiments suggest that when polyetherimides are made from appreciable amounts of 3,4'-C1PAMI and Na$_2$BPA the resulting PEI has polymer chains that are coil-shaped and that would be expected to have relatively higher modulus and lower ductility properties, as compared to PEI having a polymer chains that are more linear. As shown in FIG. 2, a stress vs. strain analysis for a polyetherimide made using C1PAMI made from a 50:50 mixture of 4-C1PA and 3-C1PA using the above sequential process has a modulus similar to that of a polyetherimide made from a 4:3 mixture of 4- and 3-C1PA, whereas a polyetherimide made using C1PAMI made from the one-pot approach 50:50 mixture of 4-C1PA and 3-C1PA has a considerably higher modulus, which can be inferred to have lower ductility.

Thus, in a method for the manufacture of the polyetherimides, a bis(halophthalimide) composition, specifically a bis(chloropthalimide) composition, is manufactured from a combination of the 4-halophthalic anhydride (6b), specifically 4-C1PA, and 3-halophthalic anhydride (6a), specifically 3-C1PA, in a ratio of 90:10 to 10:90, specifically 80:20 to 20:80, or 70:30 to 30:70, or 60:40 to 40:60. However, while a combination of the 4- and 3-halophthalic anhydride is ultimately used to form the bis(halophthalimide), all or most the of one isomer (e.g., the 4-halophthalic anhydride), is reacted with a portion of diamine (7) before the addition of the other isomer (e.g., the 3-halophthalic anhydride). At least 80 mole percent (mol %), at least 90 mole %, or 100 mole % of the total amount of a first isomer (e.g., the 4-halophthalic anhydride) is reacted with 0.5 equivalent of the diamine (7). In an embodiment, 100 mol % of the 4-halophthalic anhydride, specifically 4-C1PA, is added to 0.5 equivalent of diamine (7), specifically m-PD, o-PD, or a combination thereof in a solvent such as o-DCB, and heated until the reaction mixture is anhydrous a majority of the amic acids are converted to the imides.

The other isomer, (e.g., the 3-halophthalic anhydride) is then added, as well as diamine (7). At least 80 mol %, at least 90 mole %, or 100 mole % of the total amount of the other isomer (e.g., the 3-halophthalic anhydride) is added, together with 0.5 equivalent of the diamine (7). In an embodiment, 100 mol % of the 3-halophthalic anhydride, specifically 3-C1PA, is added to the reaction slurry containing the imides, followed by the slow addition of the 0.5 equivalent of diamine (7), specifically m-PD, o-PD, and the reaction is heated until imidization is complete.

Using this reaction sequence, the formation of the 3,4'-bis(halophthalimide) (8b) is significantly minimized. In an embodiment, the bis(halophthalimide) composition, for the example the bis(chloropthalimide) composition, contains less than 10 wt. %, less than 8 wt. %, less than 6 wt. %, less than 4 wt. %, or less than 2 wt. % of the 3,4'-bis(halophthalimide), specifically the 3,4'-bis(chlorophthalimide), based on the total weight of the bis(halophthalimide) composition. The polyetherimides can be manufactured from this composition by adding the alkali metal salt of the dihydroxy aromatic compound and polymerizing as described above.

The polyetherimides are thus manufactured from a bis(halophthalimide) composition, specifically a bis(chloropthalimide) composition, comprising the 3,3'-bis(halophthalimide) (8a), specifically 3,3'-C1PAMI, in an amount from more than 45 to less than 75 wt. %, from 45 to 55 wt. %, more specifically 50 to 70 wt. %, or 55 to 65 wt. %, based on the total weight of the bis(halophthalimide) composition.

The bis(halophthalimide) composition, specifically the bis(chloropthalimide) composition, also further comprises the 3,4'-bis(halophthalimide) (8b), specifically 3,4'-C1PAMI, in an amount of 0 or 0.1 to less than 10 wt. %, less than 8 wt. %, more specifically less than 6 wt. %, or less than 5 wt. %, or less than 3 wt. %, or less than 2 wt. %, based on the total weight of the bis(halophthalimide) composition.

Also, the bis(halophthalimide) composition, specifically the bis(chloropthalimide) composition, comprises the 4,4'-bis(halophthalimide) (8c), specifically 4,4'-C1PAMI, in an amount from more than 45 to less than 75 wt. %, from 45 to 55 wt. %, specifically 50 to 70 wt. %, or 55 to 65 wt. %, based on the weight of the bis(halophthalimide) composition.

For example, the bis(halophthalimide) composition, specifically the bis(chloropthalimide) composition, comprises from 45 to 55 weight percent of the (3,3'-bis(halophthalimide), less than 10 weight percent of the 4,3'-bis(halophthalimide), and from 45 to 55 weight percent of the 4,4'-bis(halophthalimide).

The bis(halophthalimide) composition is then polymerized with an alkali metal salt of an aromatic dihydroxy compound (9) as described above. The polyetherimides manufactured from these compositions have the —O—Z—O— groups in the polyetherimide in the 3,3', 3,4', 4,3', and 4,4' positions in the same or substantially the same ratio as in the bis(halophthalimide) compositions. In an embodiment, the polyetherimide is of formula (1)

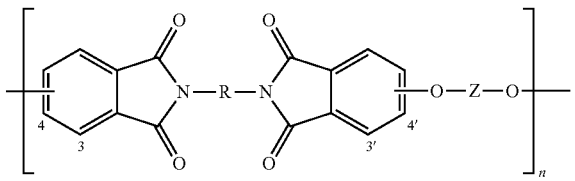

wherein n, R, and Z are as defined above. In addition, based on the total mole percent of the —O—Z—O— groups in the polyetherimide, the polyetherimides have from more than more than 45 to less than 75 mole percent of the divalent bonds of the —O—Z—O— groups in the 3,3' position, more than 0 and less than 10 mole percent of the divalent bonds of the —O—Z—O— groups in the 3,4', and 4',3 positions, and from more than 45 to less than 75 mole percent of the divalent bonds of the —O—Z—O— groups in the 4,4' position; or more than 45 to less than 55 mole percent the divalent bonds of the —O—Z—O— groups are in the 3,3' position, less than 10 mole percent of the —O—Z—O— groups are in the 3,4', and 4',3 positions, and more than 45 to less than 55 mole percent of the —O—Z—O— groups are in the 4,4' position. Other mole percents, reflective of the weight percents in the bis(halophthalimide) compositions disclosed herein, can be used. Of course, these polyetherimides can have any one or more of the properties and characteristics described herein, for example one or more of less than 3000 parts per million of a halide, based on the total parts of the polyetherimide; less than 5 weight percent of a cyclic byproduct, based on the total weight of the polyetherimide.

The compositions can further optionally comprise a reinforcing filler, for example a flat, plate-like, and/or fibrous filler. Typically, the flat, plate-like filler has a length and width at least ten times greater than its thickness, where the thickness is from 1 to 1000 micrometers (μm). Exemplary reinforcing fillers of this type include glass flakes, mica, flaked silicon carbide, aluminum diboride, aluminum flakes, and steel flakes; wollastonite comprising surface-treated wollastonite; calcium carbonate comprising chalk, limestone, marble and synthetic, precipitated calcium carbonates, generally in the form of a ground particulates; talc, comprising fibrous, modular, needle shaped, and lamellar talc; kaolin, comprising hard, soft, calcined kaolin, and kaolin comprising various coatings known in the art to facilitate compatibility with the polymeric matrix resin; mica; and feldspar.

Exemplary reinforcing fillers also include fibrous fillers such as short inorganic fibers, natural mineral fibrous fillers, single crystal fibers, glass fibers, ceramic fibers, and organic reinforcing fibrous fillers. Short inorganic fibers include, borosilicate glass, carbon fibers, and those derived from blends comprising at least one of aluminum silicates, aluminum oxides, magnesium oxides, and calcium sulfate hemihydrate. Single crystal fibers or "whiskers" include silicon carbide, alumina, boron carbide, iron, nickel, and copper single crystal fibers. Glass fibers, comprising glass fibers such as E, ECR, S, and NE glasses and quartz, and the like can also be used.

Such reinforcing fillers can be provided in the form of monofilament or multifilament fibers and can be used either alone or in combination with other types of fiber, through, for example, co-weaving or core/sheath, side-by-side, orange-type or matrix and fibril constructions, or by other methods known to one skilled in the art of fiber manufacture. Typical cowoven structures include glass fiber-carbon fiber, carbon fiber-aromatic polyimide (aramid) fiber, and aromatic polyimide fiber-glass fiber. Fibrous fillers can be supplied in the form of, for example, rovings, woven fibrous reinforcements, such as 0-90 degree fabrics, non-woven fibrous reinforcements such as continuous strand mat, chopped strand mat, tissues, papers and felts and 3-dimensionally woven reinforcements, performs and braids.

The reinforcing fibers can have a diameter of 5 to 25 micrometers, specifically diameters of 9 to 15 micrometers. In preparing molding compositions it is convenient to use reinforcing fibers such as fiberglass in the form of chopped strands of from 3 millimeters to 15 millimeters long. In articles molded from these compositions, on the other hand, shorter lengths will typically be encountered because during compounding considerable fragmentation can occur. Combinations of rigid fibrous fillers with flat, plate-like fillers can be used, for example to reduce warp of a molded article.

In some applications it can be desirable to treat the surface of the filler with a chemical coupling agent to improve adhesion to a thermoplastic resin in the composition. Examples of useful coupling agents are alkoxy silanes and alkoxy zirconates Amino, epoxy, amide, or thio functional alkoxy silanes are especially useful. Fiber coatings with high thermal stability are preferred to prevent decomposition of the coating, which could result in foaming or gas generation during processing at the high melt temperatures required to form the compositions into molded parts.

The amount of reinforcing filler used in the polyetherimide compositions can vary widely, and is that amount effective to provide the desired physical properties and flame resistance. In some instances the reinforcing filler is present in an amount from more than 10 to 60 wt. %, more specifically 15 to 40 wt. %, and even more specifically 20 to 35 wt. %, each based on the total weight of the composition.

The polyetherimide compositions can optionally further comprise one or more other types of particulate fillers. Exemplary particulate fillers include silica powder, such as fused silica and crystalline silica; boron-nitride powder and boron-silicate powders; alumina, and magnesium oxide (or magnesia); silicate spheres; flue dust; cenospheres; aluminosilicate (armospheres); natural silica sand; quartz; quartzite; perlite; tripoli; diatomaceous earth; synthetic silica; and combinations thereof. All of the above fillers can be surface treated with silanes to improve adhesion and dispersion with the polymeric matrix resin. When present, the amount of additional particulate filler in the polyetherimide composition can vary widely, and is that amount effective to provide the desired physical properties and flame resistance. In some instances the particulate filler is present in an amount from 1 to 80 wt. %, specifically 5 to 30 wt. %, more specifically 5 to 20 wt. %, each based on the total weight of the composition.

The polyetherimide compositions can include various additives ordinarily incorporated into polymer compositions of this type, with the proviso that any additive is selected so as to not significantly adversely affect the desired properties of the composition. Exemplary additives include catalysts (for example, to facilitate reaction between an impact modifier and the polyester), antioxidants, thermal stabilizers, light stabilizers, ultraviolet light (UV) absorbing additives, quenchers, plasticizers, lubricants, mold release agents, antistatic agents, visual effect additives such as dyes, pigments, and light effect additives, flame resistances, anti-drip agents, and radiation stabilizers. Combinations of additives can be used. The foregoing additives (except any fillers) are generally present in an amount from 0.005 to 20 wt. %, specifically 0.01 to 10 wt. %, based on the total weight of the composition.

Suitable antioxidants can be compounds such as phosphites, phosphonites and hindered phenols or mixtures thereof. Phosphorus-containing stabilizers comprising triaryl phosphites and aryl phosphonates are useful additives. Difunctional phosphorus containing compounds can also be unseeded. Preferred stabilizers can have a molecular weight greater than or equal to 300. Some exemplary compounds are tris-di-tert-butylphenyl phosphite available from Ciba Chemical Co. as IRGAPHOS® 168 and bis(2,4-dicumylphenyl)pentaerythritol diphosphite available commercially from Dover Chemical Co. as DOVERPHOS® S-9228.

Examples of phosphites and phosphonites include: triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,6-di-tert-butyl-4-methylphenyl)-pentaerythritoldiphosphite, diisodecyloxy pentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butyl-phenyl) 4,4'-biphenylene diphosphonite, bis(2,4-di-tert-butyl-6-methylphenyl) methyl phosphite, bis(2,4-di-tert-butyl-6-methylphenyl) ethyl phosphite, 2,2',2"-nitrilo[triethyl tris(3, 3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl)phosphite and 5-butyl-5-ethyl-2-(2,4,6-tri-tert-butylphenoxy)-1,3,2-dioxaphosphirane.

Combinations comprising more than one organophosphorous compound are contemplated. When used in combination the organophosphorous compounds can be of the same type or different types. For example, a combination can comprise two phosphites or a combination can comprise a phosphite and a phosphonite. In some embodiments, phosphorus-containing stabilizers with a molecular weight greater than or equal to 300 are useful. Phosphorus-containing stabilizers, for example an aryl phosphite, may be present in the composition in an amount from 0.005 to 3 wt. %, specifically 0.01 to 1.0 wt. %, based on total weight of the composition.

Hindered phenols can also be used as antioxidants, for example alkylated monophenols, and alkylated bisphenols or polyphenols. Exemplary alkylated monophenols include 2,6-di-tert-butyl-4-methylphenol; 2-tert-butyl-4,6-dimethylphenol; 2,6-di-tert-butyl-4-ethylphenol; 2,6-di-tert-butyl-4-n-butylphenol; 2,6-di-tert-butyl-4-isobutylphenol; 2,6-dicyclopentyl-4-methylphenol; 2-(alpha-methylcyclohexyl)-4,6-dimethylphenol; 2,6-dioctadecyl-4-methylphenol; 2,4,6-tricyclohexylphenol; 2,6-di-tert-butyl-4-methoxymethylphenol; nonyl phenols which are linear or branched in the side chains, for example, 2,6-di-nonyl-4-methylphenol; 2,4-dimethyl-6-(1'-methylundec-1'-yl)phenol; 2,4-dimethyl-6-(1'-methylheptadec-1'-yl)phenol; 2,4-dimethyl-6-(1'-methyltridec-1'-yl)phenol and mixtures thereof. Exemplary alkylidene bisphenols include 2,2'-methylenebis(6-tert-butyl-4-methylphenol), 2,2'-methylenebis(6-tert-butyl-4-ethylphenol), 2,2'-methylenebis[4-methyl-6-(alpha-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(alpha-methylbenzyl)-4-nonylphenol], 2,2'-methylenebis[6-(alpha, alpha-dimethylbenzyl)-4-nonylphenol], 4,4'-methylenebis-(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy-2-methylphenyl)-4-n-dodecylmercaptobutane, 1,1,5,5-tetra-(5-tert-butyl-4-hydroxy-2-methylphenyOpentane and mixtures thereof.

The hindered phenol compound can have a molecular weight of greater than or equal to 300 g/mole. The high molecular weight can help retain the hindered phenol moiety in the polymer melt at high processing temperatures, for example greater than or equal to 300° C. Hindered phenol stabilizers, are usually present in the composition in an amount from 0.005 to 2 wt. %, specifically 0.01 to 1.0 wt. %, based on total weight of the composition.

Examples of mold release agents include both aliphatic and aromatic carboxylic acids and their alkyl esters, for example, stearic acid, behenic acid, pentaerythritol tetrastearate, glycerin tristearate, and ethylene glycol distearate. Polyolefins such as high-density polyethylene, linear low-density polyethylene, low-density polyethylene and similar polyolefin homopolymers and copolymers can also be used a mold release agents. Mold release agents are typically present in the composition at 0.05 to 10 wt. %, based on total weight of the composition, specifically 0.1 to 5 wt. %. Preferred mold release agents will have high molecular weight, typically greater than 300, to prevent loss of the release agent from the molten polymer mixture during melt processing.

In particular, an optional polyolefin can be added to modify the chemical resistance characteristics and mold release characteristics of the composition. Homopolymers such as polyethylene, polypropylene, polybutene can be used either separately or in combination. Polyethylene can be added as high-density polyethylene (HDPE), low-density polyethylene (LDPE) or branched polyethylene. Polyolefins can also be used in copolymeric form with compounds containing carbonic acid radicals such as maleic acid or citric acid or their anhydrides, acid compounds containing acrylic acid radicals such as acrylic acid ester, and the like, as well as combinations comprising at least one of the foregoing. When present, the polyolefin, in particular HDPET, is used in an amount from more than 0 to 10 wt. %, specifically 0.1 to 8 wt. %, more specifically from 0.5 to 5 wt. %, all based on the total weight of the composition.

In some embodiments, the compositions can further include at least one additional polymer. Examples of such additional polymers include and are not limited to PPSU (polyphenylene sulfone), polyetherimides, PSU (polysulfone), PPET (polyphenylene ether), PFA (perfluoroalkoxy alkane), MFA (co-polymer of TFE tetrafluoroethylene and PFVE perfluorinated vinyl ether), FEP (fluorinated ethylene propylene polymers), PPS (poly(phenylene sulfide), PTFE (polytetrafluoroethylene), PA (polyamide), PBI (polybenzimidizole) and PAI (poly(amide-imide)), poly(ether sulfone), poly(aryl sulfone), polyphenylenes, polybenzoxazoles, polybenzthiazoles, as well as blends and co-polymers thereof. When present, the polymer is used in an amount from more than 0 to 20 wt. %, specifically 0.1 to 15 wt. %, more specifically from 0.5 to 10 wt. %, all based on the total weight of the composition. In an embodiment, no polymer other than the polyetherimide as described herein is present in the composition.

Colorants such as pigment and/or dye additives can also optionally be present. Useful pigments can include, for example, inorganic pigments such as metal oxides and mixed metal oxides such as zinc oxide, titanium dioxide, iron oxides, or the like; sulfides such as zinc sulfides, or the like; aluminates; sodium sulfo-silicates sulfates, chromates, or the like; carbon blacks; zinc ferrites; ultramarine blue; organic pigments such as azos, di-azos, quinacridones, perylenes, naphthalene tetracarboxylic acids, flavanthrones, isoindolinones, tetrachloroisoindolinones, anthraquinones, enthrones, dioxazines, phthalocyanines, and azo lakes; Pigment Red 101, Pigment Red 122, Pigment Red 149, Pigment Red 177, Pigment Red 179, Pigment Red 202, Pigment Violet 29, Pigment Blue 15, Pigment Blue 60, Pigment Green 7, Pigment Yellow 119, Pigment Yellow 147, Pigment Yellow 150, and Pigment Brown 24; or combinations comprising at least one of the foregoing pigments. Pigments are generally used in amount from 0 to 10 wt. %, specifically 0 to 5 wt. %, based on the total weight of the composition. In some instances, where improved impact is desired pigments such as titanium dioxide will have a mean particle size of less than 5 μm.

The composition can also optionally include a fluoropolymer in an effective amount to provide anti-drip or other beneficial properties to the resin composition. In one instance the fluoropolymer is present in an amount 0.01 to 5.0 wt. % of the composition. Examples of suitable fluoropolymers and methods for making such fluoropolymers are set forth, for example, in U.S. Pat. Nos. 3,671,487, 3,723,373, and 3,383,092. Suitable fluoropolymers include homopolymers and copolymers that comprise structural units derived from one or more fluorinated alpha-olefin monomers, for example, $CF_2=CF_2$, $CHF=CF_2$, $CH_2=CF_2$ and $CH_2=CHF$ and fluoro propylenes such as, for example, $CF_3CF=CF_2$, $CF_3CF=CHF$, $CF_3CH=CF_2$, $CF_3CH=CH_2$, $CF_3CF=CHF$, $CHF_2CH=CHF$ and $CF_3CF=CH_2$.

Copolymers comprising structural units derived from two or more fluorinated alpha-olefin monomers can also be used, for example poly(tetrafluoroethylene-hexafluoroethylene), as well as copolymers comprising structural units derived from one or more fluorinated monomers and one or more non-fluorinated monoethylenically unsaturated monomers that are copolymerizable with the fluorinated monomers such as poly(tetrafluoroethylene-ethylene-propylene) copolymers. Suitable non-fluorinated monoethylenically unsaturated monomers include for example, alpha-olefin monomers such as ethylene, propylene, butene, acrylate monomers such as, methyl methacrylate, butyl acrylate, and the like, with poly(tetrafluoroethylene) homopolymer (PTFE) preferred.

The fluoropolymer can be pre-blended in some manner with a polymer such as an aromatic polycarbonate or polyetherimide resin. For example, an aqueous dispersion of fluoropolymer and a polycarbonate resin can be steam precipitated to form a fluoropolymer concentrate for use as a drip inhibitor additive in thermoplastic resin compositions, as disclosed, for example, in U.S. Pat. No. 5,521,230. Alternatively, the fluoropolymer can be encapsulated.

In some instances it is desired to have polyetherimide compositions that are essentially free of bromine and chlorine. "Essentially free" of bromine and chlorine means that the composition has less than 3 wt. % of bromine and chlorine, and in other embodiments less than 1 wt. % bromine and chlorine by weight of the composition. In other embodiments, the composition is halogen free. "Halogen free" is defined as having a halogen content (total amount of fluorine, bromine, chlorine and iodine) of less than or equal to 1000 parts by weight of halogen per million parts by weight of the total composition (ppm). The amount of halogen can be determined by ordinary chemical analysis such as atomic absorption.

The polyetherimide compositions can be prepared by blending the ingredients under conditions for the formation of an intimate blend. Such conditions often include melt mixing in single or twin screw type extruders, mixing bowl, or similar mixing devices that can apply a shear to the components. Twin-screw extruders are often preferred due to their more intensive mixing capability and self-wiping capability, over single screw extruders. It is often advantageous to apply a vacuum to the blend through at least one vent port in the extruder to remove volatile impurities in the composition. Often it is advantageous to dry the polyetherimide polymers prior to melting. The melt processing is often performed at 320 to 380° C. to avoid excessive polymer degradation while still allowing sufficient melting to get an intimate polymer mixture free of any unbelted components. The polymer blend can also be melt filtered using a 40 to 100 micrometer candle or screen filter to remove undesirable black specks or other heterogeneous contaminants.

In an exemplary process, the various components are placed into an extrusion compounder to produce a continuous strand that is cooled and then chopped into pellets. In another procedure, the components are mixed by dry blending, and then fluxed on a mill and comminuted, or extruded and chopped. The composition and any optional components can also be mixed and directly molded, e.g., by injection or transfer molding techniques. Preferably, all of the components are freed from as much water as possible. In addition, compounding is carried out to ensure that the residence time in the machine is short; the temperature is carefully controlled; the friction heat is utilized; and an intimate blend between the components is obtained.

The composition can then be molded in any equipment conventionally used for thermoplastic compositions, such as a Newbury or van Dorn type injection-molding machine with conventional cylinder temperatures, at 350° C. to 400° C., and conventional mold temperatures at 100° C. to 170° C.

The physical properties of the when the polyetherimide composition can be varied to achieve the desired performance properties.

The polyetherimides manufactured using the bis(halophthalimide) compositions as described above can have a heat deflection temperature (HDT) of at least 190° C., specifically at least 200° C., at least 218° C., more specifically at least 230° C., determined using DMA in on a film sample.

Also, the polyetherimides can have a heat deflection temperature at least 10° C. higher, specifically at least 12° C. higher, more specifically at least 14° C. higher than a heat deflection temperature of the same polyetherimide manufactured using a bis(halophthalimide) composition comprising more than 10 wt. % of the 3,4'-bis(halophthalimide), each determined using dynamic mechanical analysis (DMA) on a film sample.

In addition, the polyetherimides can have at least 10% lower, at least 15% lower, more specifically at least 20% lower stiffness than a stiffness of the same polyetherimide manufactured using a bis(halophthalimide) composition comprising more than 10 wt. % of the 3,4'-bis(halophthalimide), each determined by DMA over 30° C. to 110° C. on a film sample.

Also, the polyetherimides can have a ratio of a low shear rate viscosity to a high shear rate viscosity that is at least 30% higher, specifically at least 35% higher, more specifically at least 40% higher than the same ratio of the same polyetherimide manufactured using the bis(halophthalimide) composition comprising more than 10 wt. % of the 3,4'-bis(halophthalimide) and more than 55 weight percent of the 4,4'-bis(chlorophthalimide), each determined by parallel plate rheometry.

The polyetherimides manufactured using the above-described bis(halophthalimide) composition can comprise, based on parts by weight of the polyetherimide, less than 3000 parts per million (ppm), less than 2000 ppm, specifically less than 1500 ppm, more specifically less than 1000 ppm of chloride.

In a further advantageous feature, the polyetherimides can have reduced levels of cyclic byproducts arising from the intramolecular reaction of the alkali metal salt (9) and the bis(halophthalimide)s (8). In an embodiment, the polyetherimides manufactured as described above comprise, based on parts of the polyetherimide, less than 5 wt. %, specifically less than 3 wt. %, more specifically less than 1.5 wt. % of the cyclic byproducts of the alkali metal salt (9) and the bis (halophthalimide) (8), specifically the bis(chlorophthalimide).

The polyetherimides can have a weight average molecular weight (Mw) of 5,000 to 100,000 grams per mole (g/mole) as measured by gel permeation chromatography (GPC). In some embodiments the Mw can be 10,000 to 80,000. The molecular weights as used herein refer to the absolute weight averaged molecular weight (Mw), referenced to polystyrene standards.

The polyetherimides can have an intrinsic viscosity greater than or equal to 0.2 deciliters per gram (dl/g) as measured in m-cresol at 25° C. Within this range the intrinsic viscosity can be 0.35 to 1.0 dl/g, as measured in m-cresol at 25° C.

The polyetherimides can have a glass transition temperature greater than 180° C., specifically 200° C. to 315° C., as measured using differential scanning calorimetry (DSC) per American Society for Testing Materials (ASTM) test D3418. In an embodiment the polyetherimide has a glass transition temperature of 220 to 240° C.

The polyetherimides can have a melt index of 0.1 to 10 grams per minute (g/min), as measured by ASTM DI 238 at 320 to 370° C., more specifically 337° C. using a 6.1 kilogram (kg) weight.

In some embodiments the polyetherimides have a melt viscosity of 50 to 20,000 Pascal-seconds, 100 to 15,000 Pascal-seconds, or more specifically, 200 to 10,000 Pascal-seconds at 400° C. as measured by ASTM method D3835 using a capillary rheometer with a shear rate of 100 to 10,000 1/sec.

The composition can have a tensile strength greater than or equal to 90 MPa, specifically 90 To 120 MPa, measured in accordance with ASTM D648.

The polyetherimide composition can have a melt flow rate (MFR) at 337° C. of greater than 10 grams per 10 minutes, when measured in accordance with ASTM D1238 at 337° C. using a 6.1 Kg weight.

Also disclosed are articles comprising the above-described polyetherimide compositions. The article can be a sheet, film, multilayer sheet, multilayer film, molded part, extruded profile, coated part, or fiber. Also, the article can be a molded part having a thickness from 0.1 to 100 mm, specifically 1 to 10 mm, more specifically 1 to 5 mm.

The polyetherimide compositions can be formed into articles by any number of methods, for example, shaping, extruding (including profile extrusion), thermoforming, or molding, including injection molding, compression molding, gas assist molding, structural foam molding, and blow molding. In one embodiment a method of forming an article comprises shaping, extruding, blow molding, or injection molding the composition to form the article. Polyetherimide compositions can also formed into articles using thermoplastic processes such as film and sheet extrusion, for example melt casting, blown film extrusion and calendaring. Co-extrusion and lamination processes can be used to form composite multi-layer films or sheets.

Examples of applications include: food service, medical, lighting, lenses, sight glasses, windows, enclosures, safety shields, and the like. The high melt flow allows the composition to be molded into intricate parts with complex shapes and/or thin sections and long flow lengths. Examples of other articles include, but are not limited to, cookware, medical devices, trays, plates, handles, helmets, animal cages, electrical connectors, enclosures for electrical equipment, engine parts, automotive engine parts, lighting sockets and reflectors, electric motor parts, power distribution equipment, communication equipment, computers and the like, comprising devices that have molded in snap fit connectors. The polyetherimide compositions can also be made into film and sheet as well as compositions of laminate systems. Other articles include, for example, fibers, sheets, films, multilayer sheets, multilayer films, molded parts, extruded profiles, coated parts and foams: windows, luggage racks, wall panels, chair parts, lighting panels, diffusers, shades, partitions, lenses, skylights, lighting devices, reflectors, ductwork, cable trays, conduits, pipes, cable ties, wire coatings, electrical connectors, air handling devices, ventilators, louvers, insulation, bins, storage containers, doors, hinges, handles, sinks, mirror housing, mirrors, toilet seats, hangers, coat hooks, shelving, ladders, hand rails, steps, carts, trays, cookware, food service equipment, communications equipment and instrument panels.

The compositions are especially useful for articles such as reflectors, e.g., automobile reflectors, an optical lens, a fiber optic connector, and an adhesive. Where the compositions are used an adhesive, the article comprises a first substrate having a first surface, a second substrate having a second surface, and a layer of a polymer composition comprising the polyetherimide disposed between and in contact with the first surface and the second surface. For example, the adhesive can be used to adhere two polymer substrates, two metal substrates, or a metal substrate and a polymer substrate. There is no particular limitation as to the type of metals or polymers in the substrates. In an embodiment, the adhesive is especially useful in an article having a metal substrate and a fluoropolymer substrate (such as polytetrafluoroethylene (PTFE)) substrate, and an adhesive composition comprising the poly(etherimide)

disposed between a surface of the metal substrate and a surface of the fluoropolymer substrate. In a specific embodiment, an article comprises (i) a polytetrafluoroethylene substrate having a first surface, (ii) a metal substrate having a second surface, and (iii) the polymer composition of claim 1, situated between the polytetrafluoroethylene substrate and the metal substrate. The adhesive layer containing the polymer composition can be in direct contact with the surfaces of the adherends, or an additional layer can be present, for example a primer.

Without further elaboration, it is believed that one skilled in the art can, using the description herein, utilize the present invention. The following examples are included to provide additional guidance to those skilled in the art of practicing the claims. Accordingly, these examples are not intended to limit the invention in any manner.

EXAMPLES

The materials used in the Examples are shown in Table 1.

Preparation Procedure for a mixture of 3,3'-ClPAMI, 3,4'-ClPAMI, and 4,4'-ClPAMI for inventive examples 1-2.

A 250-mL, three-necked flask equipped with a stopper and a gas valve were charged with 1.5 grams (0.0138 moles) of mPD, 5.157 grams (0.0277 moles) 4-ClPA, 0.011 grams (0.1 mmoles) of SPP, and 60 grams of oDCB. The flask was then equipped with a stir shaft and bearing, nitrogen adapter, and a Dean Stark trap receiver topped with a reflux condenser. A gentle sweep of nitrogen was established through the headspace of the vessel. The stirring was initially done at 100 revolutions per minute (rpms) to prevent splattering. The reaction was then heated to 100° C. and then ramped slowly to 200° C. over about 60 minutes. The temperature ramp was to 150° C., 180° C., and 200° C. Once the imidization was nearly complete, i.e., less than 1 mole percent amide-acids by HPLC analysis (approximately 3 hours). The three-necked flask was then charged with 5.157 grams (0.0277 moles) 3-ClPA and after all the 3-ClPA was added then 1.5 grams (0.0138 moles) of mPD was slowly added over 30 minutes with another 60

TABLE 1

| Material | Chemical Description | Source |
|---|---|---|
| ClPAMI Mixture 1 | | |
| 47% 3,3'-ClPAMI | 1,3-bis[N-(3-chlorophthalimido)]benzene | SABIC INNOVATIVE PLASTICS |
| 7% 3,4'-ClPAMI | 1,3-[N-(4-chlorophthalimido)][N-(3-chlorophthalimido)]benzene | |
| 46% 4,4'-ClPAMI | 1,3-bis[N-(4-chlorophthalimido)]benzene | |
| ClPAMI Mixture 2 | | |
| 71% 3,3'-ClPAMI | 1,3-bis[N-(3-chlorophthalimido)]benzene | SABIC INNOVATIVE PLASTICS |
| 8% 3,4'-ClPAMI | 1,3-[N-(4-chlorophthalimido)][N-(3-chlorophthalimido)]benzene | |
| 21% 4,4'-ClPAMI | 1,3-bis[N-(4-chlorophthalimido)]benzene | |
| ClPAMI Mixture 3 | | |
| 1% 3,3'-ClPAMI, | 1,3-bis[N-(3-chlorophthalimido)]benzene | SABIC INNOVATIVE PLASTICS |
| 9% 3,4'-ClPAMI, | 1,3-[N-(4-chlorophthalimido)][N-(3-chlorophthalimido)]benzene | |
| 90% 4,4'-ClPAMI | 1,3-bis[N-(4-chlorophthalimido)]benzene | |
| ClPAMI Mixture 4 | | |
| 25% 3,3'-ClPAMI | 1,3-bis[N-(3-chlorophthalimido)]benzene | SABIC INNOVATIVE PLASTICS |
| 50% 3,4'-ClPAMI | 1,3-[N-(4-chlorophthalimido)][N-(3-chlorophthalimido)]benzene | |
| 25% 4,4'-ClPAMI | 1,3-bis[N-(4-chlorophthalimido)]benzene | |
| MPD | meta-Phenylene diamine | DuPont |
| 4-ClPA | 4-Chlorophthalic anhydride | SABIC INNOVATIVE PLASTICS |
| 3-ClPA | 3-Chlorophthalic anhydride | SABIC INNOVATIVE PLASTICS |
| $H_3PO_4$ | Phosphoric acid | Fischer |
| $Na_2BPA$ | Disodium Bisphenol A | SABIC INNOVATIVE PLASTICS |
| oDCB | ortho-Dichlorobenzene | Fischer |
| SPP | Sodium Phenyl Phosphinate | Fisher |
| HEGCl | Hexaethylguanidinium chloride | Atul |

Techniques and Procedures

GPC Testing Procedure

The GPC samples were prepared by dissolving 5-10 mg of a sample in 10 mL of dichloromethane. Three to five drops of the polymer solution was added to a 10 mL dichloromethane solution with acetic acid (1-2 drops). The sample solution was then filtered and the analysis was performed by referencing the polymer peak to the oDCB peak. The instrument was a Waters 2695 separations module, which was calibrated with polystyrene standards from Aldrich chemical company. The cyclics were analyzed by slicing the GPC traces for cyclics n=2 and 3, but the cyclic n=1 was resolved well enough that it could be integrated separately.

grams of oDCB. The stirring was increased to 300 rpms once the sticky phase was finished. The oDCB was removed from the mixture until it reached 22 wt % solids (approximately 10 grams of oDCB). After 2 to 3 hours a sample was taken: 30 mg in 20 mL of acetonitrile (sonicated 15 minutes and filtered) and analyzed by HPLC calibrated for monoamine (monoamine is the mono-imide of halo-phthalic anhydride with a diamine as MPD), 4-ClPA, and mPD. Once the amounts of analytes are known the appropriate correction to the stoichiometry of the reaction was made from either mPD or 4-ClPA. This repeated until the 3-monoamine, 4-monoamine, 3-ClPA and 4-ClPA was within the specified limit of the reaction, 0.2 mole percent. The reaction was then cooled and kept under a static nitrogen atmosphere.

A similar procedure can be used to prepare the C1PAMI isomers separately.

Preparation Procedure for a Mixture of 3,3'-C1PAMI, 3,4'-C1PAMI, and 4,4'-C1PAMI for Comparative Examples 3-4

A 250-mL, three-necked flask equipped with a stopper and a gas valve were charged with 3.0 grams (0.0275 moles) of mPD, 5.052 grams (0.0275 moles) 4-C1PA, 5.052 grams (0.0275 moles) of 3-C1PA, 0.011 grams (0.1 mmoles) of SPP, and 60 grams of oDCB. The flask was then equipped with a stir shaft and bearing, nitrogen adapter, and a Dean Stark trap receiver topped with a reflux condenser. A gentle sweep of nitrogen was established through the headspace of the vessel. The reaction was then heated to 100° C. and then ramped slowly to 200° C. The temperature ramp was to 150° C., 180° C., and 200° C. The oDCB was removed from the mixture until it reached 20-50 wt % solids (20 grams approximately of oDCB). The random mixture of C1PA generates a 1:2:1 ratio of 3,3'-C1PAMI, 3,4'-C1PAMI, and 4,4'-C1PAMI respectively. The high concentration of 3,4'-C1PAMI allows for higher wt % solids to be achieved than the normal 4,4'-C1PAMI reaction at 20% solids, because the solubility of the 3,4'-isomer was better than the other two isomers. Reactions as high as 50% solids can be achieved on the lab scale. After 2 to 3 hours a sample was taken: 30 mg in 20 mL of acetonitrile (sonicated 15 minutes and filter) and analyzed by HPLC calibrated for monoamine, 4-C1PA, and mPD. Once the amounts of analytes are known the appropriate correction was made from either mPD or 4-C1PA. This repeated until the 3-monoamine, 4-monoamine, 3-C1PA and 4-C1PA was within the specification limit of the reaction, 0.2 mole percent. The reaction was then cooled and stoppered.

A similar procedure can be used to prepare the C1PAMI isomers separately.

Polymerization Procedure

Polyetherimides were made as follows. Once the mixture of 3,3'-C1PAMI, 3,4'-C1PAMI, and 4,4'-C1PAMI isomers were made, the reaction vessel was then transferred to a dry box where the salt of 7.35 grams (0.0270 moles) of Na$_2$BPA was added. The reaction was then heated to 200° C. with a nitrogen gentle sweep, to remove some oDCB from the mixture until it reached 30-50 wt % solids (20-40 grams approximately of oDCB). Once the overheads were dry by Karl Fischer analysis (<50 ppm), 71 mg (1 mole %) of HEGC1 was charged to the solution; within 30 minutes the solution became brownish and finally a golden solution after 90 minutes. The mixture was sampled after 2 hours to measure Mw, then the Mw analysis was repeated every hour until the reaction plateaued (plateau=3 samples within 300 atomic mass units (amu)). If the Mw was below 45,000 a correction of Na$_2$BPA was made. The reaction was then quenched with 134 mg (1 mole % respect to polymer) of H$_3$PO$_4$ (85% aqueous) concentrated. Once the acid was added a nitrogen purge was added to remove any water (5 minutes). The reaction was heated for another hour. The reaction was then cooled and diluted to 10 wt % with oDCB (approximately 70 mL). The mixture was then filtered on Buchner funnel using a Whatman 1 micrometer glass filter disk. The golden solution was then transferred to 1-liter separatory funnel with equal volume of acidic water and vigorously shaken. Once the golden polymer solution had phase split it was transferred to a blender with an equal volume of hexane and blended. The mixture was filtered and dried under vacuum at 165° C. for 24 hours.

Sample Preparation for Property Testing

Test parts were injection molded on a 180-ton molding machine with a set temperature of approximately 360-400° C. The pellets were dried for 3-4 hours at 120° C. in a forced air circulating oven prior to injection molding.

Testing Procedures

Glass transition temperature (Tg) was measured on a 10 mg sample at heating rate of 20° C./min.

DMA was determined in accordance with following procedure. The films samples (thickness=0.5 mm to 2 mm) were mounted on the grips and test was done under tensile mode at 1 Hz frequency and with 2° C./min ramp rate. The storage modulus was recorded as function of temperature. The heat distortion was calculated using the method described on pages 1104-1109, Issue 15, Vol. 19, November 1979, of Polymer Engineering.

Residual Testing Procedure

The residual amount of C1PAMI and PAMI were analyzed by HPLC analysis from the fractionated lows from polymer: no PAMI and less than 200 ppm of C1PAMI could be detected. The fractionated lows were prepared by dissolving 1 gram of PEI into methylene chloride. Then 5 mL of acetonitrile was added to the PEI solution, which was then filter with 0.6 micrometer filter. The filtered liquor was then analyzed by LC on a Waters 2695 separations module HPLC instrument, which was calibrated with PAMI and C1PAMI isomers.

Rheology Testing Procedure

The viscosity data in Example 4 was measured using parallel plate rheometry, and ratio of viscosities at 1 rad/s to 100 radian/sec was measured at a 350° C. This viscosity ratio gives a measure of shear thinning or improved flow properties. The higher the viscosity ratio, the higher is the shear thinning and hence improved flow.

Examples 1-4

The purpose of Examples 1-4 was to evaluate the effect of different C1PAMI isomer ratios on the properties of polyetherimides made from a C1PAMI mixture containing more than 45 wt % 3,3'-C1PAMI and less than 10 wt % 3,4'-C1PAMI, compared to polyetherimides made from a C1PAMI mixture containing less then 45 wt % 3,3'-C1PAMI and greater than 10 wt % 3,4'-chloro PAMI. The C1PAMI mixtures were each made using at least 50% 3-C1PA.

Accordingly, four polyetherimides were prepared in accordance to the procedures above, using the C1PAMI compositions shown in Table 2.

The polymers prepared as described above were targeted for a weight average molecular weight (Mw) of 55,000 Daltons (polystyrene standards were used for calibration). Table 2 shows a summary of the molecular weight of the polyetherimides of Examples 1-4 as determined by GPC.

The resulting polyetherimides were also tested for one or more of Tg, HDT, Vicat, stiffness (as indicated by storage modulus), and flow (as indicated by the rheology ratio), using the methods described above. The results are shown in Table 2.

TABLE 2

|  | Example 1 (Inventive) | Example 2 (Inventive) | Example 3 (Comparative) | Example 4 (Comparative) |
|---|---|---|---|---|
| Isomer in ClPAMI mixture (Wt %) | | | | |
| 3,3'-ClPAMI | 47 | 71 | 1 | 25 |
| 3,4'-ClPAMI | 7 | 8 | 9 | 50 |
| 4,4'-ClPAMI | 46 | 21 | 90 | 25 |
| Properties | | | | |
| Mw (amu) | 52929 | 50617 | 54260 | 54027 |
| Mn (amu) | 22031 | 20510 | 22608 | 19837 |
| Polydispersity Index (PDI) | 2.4 | 2.47 | 2.4 | 2.72 |
| Tg (° C.) | 224 | 229 | 219 | 229 |
| HDT (° C.) (0.44 MPa) | 218 | 220 | 207 | 218 |
| HDT (° C.) (1.8 MPa) | NA | NA | 192 | 202 |
| Vicat (° C.) | NA | NA | 216 | 226 |
| Rheology Ratio | 3.0 | 3.0 | 2.0 | 3.0 |
| Storage Modulus (Mpa) | | | | |
| Temperature (° C.) | | | | |
| 30 | 2365 | 2394 | 2550 | 2680 |
| 40 | 2326 | 2381 | 2452 | 2586 |
| 50 | 2289 | 2357 | 2264 | 2429 |
| 60 | 2246 | 2339 | 2098 | 2307 |
| 70 | 2198 | 2315 | 1976 | 2214 |
| 80 | 2142 | 2271 | 1925 | 2163 |
| 90 | 2049 | 2178 | 1961 | 2178 |
| 100 | 1828 | 1868 | 1992 | 2260 |
| 110 | 1863 | 1817 | 1287 | 2184 |

Results and Discussion

As can be seen from the results in Table 2, the molecular weights of all four Examples were similar. Examples 1 and 2

Inventive Example 1 shows that when PEI was made from a ClPAMI mixture containing at least 47 wt % 3,3'-ClPAMI, at least 46 wt % 4,4'-ClPAMI, and a maximum of 7 wt % of 3,4'-ClPAMI, the resulting PEI had a Tg of at least 224° C., an HDT of at least 218 C.

Inventive Example 2 shows that when the PEI was made from a ClPAMI mixture with at least 71 wt % 3,3'-ClPAMI, at least 20 wt % 4,4'-ClPAMI, and less than 9 wt % 3,4'-ClPAMI, the resulting PEI had a Tg of at least 224° C., an HDT of at least 218° C.

Comparative Example 3 shows that when the PEI was made from a ClPAMI mixture containing less than 2 wt % 3,3'-ClPAMI and less than 10 wt % 3,4'-ClPAMI, the resulting PEI had a Tg of 219° C. (10° C. lower than Examples 1 and 2). The HDT of comparative Example 3 is at least 10 C lower than inventive Example 1 and 2.

Comparative Example 4 shows that when the PEI was made from a mixture containing at least 25 wt % of 3,3'-ClPAMI and at least 50 wt % of 3,4'-ClPAMI, the resulting PEI had a Tg of at least 229° C. and an HDT of at least 218° C.

Taken together, the above results show that Inventive Examples 1 and 2 had a Tg of at least 224° C. an HDT at least 218 C. Thus, when PEI is made from a ClPAMI mixture containing 45-75 wt % 3,3'-ClPAMI, 45-75 wt % 4,4'-ClPAMI, and less than 10 wt % of 3,4'-ClPAMI, the resulting PEI had a Tg of at least 224° C. an HDT of at least 218 C. Still further, Inventive Examples 1 and 2 had a rheology ratio (flow) of 3.0. This result is in contrast to Comparative Example 3, which had a rheology ratio of 2.0, and comparable to the flow of Comparative Example 4. Thus, PEI made from a ClPAMI mixture containing 45-75 wt % 3,3'-ClPAMI, 45-75 wt % 4,4'-ClPAMI, and less than 10 wt % of 3,4'-ClPAMI has at least 30% higher flow than a PEI made from a ClPAMI mixture containing greater than 55, or greater than 75 wt % 4,4'-ClPAMI and less than 10 wt % 3,4'-ClPAMI. Alternatively, PEI made from a ClPAMI mixture containing 45-75 wt % 3,3'-ClPAMI, 25-55 wt % 4,4'-ClPAMI, and less than 10 wt % of 3,4'-ClPAMI has at least 30% higher flow than a PEI made from a ClPAMI mixture containing greater than 55, or greater than 75 wt % 4,4'-ClPAMI and less than 10 wt % 3,4'-ClPAMI.

The results also show that Inventive Examples 1 and 2 have lower stiffness over a temperature range of 30° C. to 110° C., compared to Comparative Example 4. Thus, PEI made from a ClPAMI mixture containing 45-75 wt % 3,3'-ClPAMI, 45-75 wt % 4,4'-ClPAMI, and less than 10 wt % of 3,4'-ClPAMI has at least 30% lower stiffness over a temperature range from 30° C. to 110° C. than a PEI made from a ClPAMI mixture having greater than 10 wt % 3,4'-chloro PAMI.

In summary, Inventive Examples 1 and 2, are made from a ClPAMI mixture containing 45-75 wt % 3,3'-ClPAMI, 45-75 wt % 4,4'-ClPAMI, and less than 10 wt % of 3,4'-ClPAMI, demonstrated an HDT of at least 218° C., possessed stiffness similar to Comparative Example 3, and also maintained the flow and Tg of Comparative Example 4.

Example 5

A Projector Reflector article is molded with PEI having the properties of EXAMPLE 2), using a 75 Ton Sumitomo injection molding machine. The temperature settings were between 670-710° F. (354-377° C.), and an injection pressure ranging from 14500 psi to 17500 psi is used. The dimensions of the article are approximately 64 mm high and 100 mm wide, with a wall thickness of 3 to 4 mm.

The article has qualitatively good surface aesthetics, no splay, no cracking during injection molding of the part. The article can be directly metallized with aluminum such that when it is metallized, the article exhibits excellent reflectance of at least 90%. Due to the improved ductility our composition imparts to the article, our results show that reflectors having thin walls, resistant to cracking, can now be made.

All patents and references cited herein are incorporated by reference.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A method for the manufacture of a bis(halophthalimide) composition from a combination of a 4-halophthalic anhydride isomer of the formula

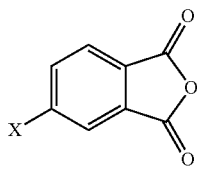

and a 3-halophthalic anhydride isomer of the formula

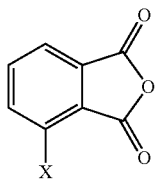

wherein X is a halogen, in a ratio of the 4-halophthalic anhydride to 3-halophthalic anhydride of 90:10 to 10:90, and wherein one of the isomers is a first isomer and the other is a second isomer, the method comprising reacting at least 80 mole percent of the total amount of the first isomer with a diamine of the formula $H_2N$—R—$NH_2$ wherein R is selected from an aromatic hydrocarbon group having 6 to 30 carbon atoms, a halogenated derivative thereof, a straight or branched chain alkylene group having 2 to 10 carbon atoms, a cycloalkylene group having 3 to 20 carbon atoms, or a divalent group of the formula

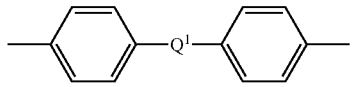

wherein $Q^1$ is selected from —O—, —S—, —C(O)—, —$SO_2$—, —SO—, —$C_yH_{2y}$— wherein y is 1 to 5, and a halogenated derivative thereof, to form a bis(halophthalimide) to form a reaction mixture comprising a bis(halophthalimide); and adding the second isomer and 0-20 mole percent of the total amount of the first isomer and another portion of the diamine to the reaction mixture, to form a bis(halophthalimide) composition comprising, based on the total weight of the composition, from more than 45 to less than 75 weight percent of a 3,3'-bis(halophthalimide) of the formula

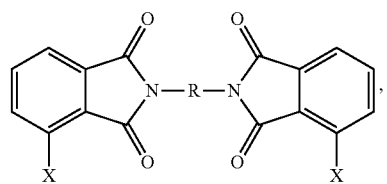

less than 10 weight percent of a 4,3'-bis(halophthalimide) of the formula

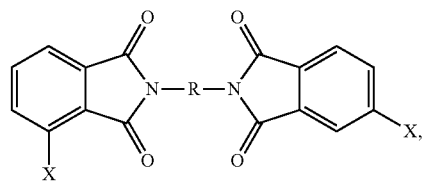

and from more than 45 to less than 75 weight percent of a (4,4'-bis(halophthalimide) of the formula

wherein X and R are as defined above.

2. The method of claim 1, wherein X is chlorine.

3. The method of claim 1, wherein
X is chlorine; and
R is a divalent group of formula

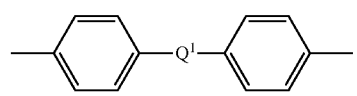

wherein $Q^1$ is —O—, —S—, —C(O)—, —$SO_2$—, —SO—, or —$C_yH_{2y}$— wherein y is an integer from 1 to 5.

4. The method of claim 1, wherein Z is 2,2-(4-phenylene) isopropylidene and R is m-phenylene, p-phenylene, p-phenylene diarylsulfone, or a combination thereof.

5. The method of claim 1, wherein the bis(halophthalimide) composition comprises
from 45 to less than 55 weight percent of the (3,3'-bis(halophthalimide),
less than 10 weight percent of the 3,4'-bis(halophthalimide), and
from 45 to 55 weight percent of the 4,4'-bis(halophthalimide).

6. A method for the manufacture of a polyetherimide composition, the method comprising:
forming a bis(halophthalimide) composition according to the method of claim 1;
reacting, in the presence of a catalytically active amount of a phase transfer catalyst, an alkali metal salt of a dihydroxy aromatic compound of the formula

MO—Z—OM wherein M is an alkali metal salt and Z is an aromatic $C_{6-24}$ monocyclic or polycyclic moiety optionally substituted with 1 to 6 $C_{1-8}$ alkyl groups, 1 to 8 halogen atoms, or a combination thereof, with the bis(halophthalimide) composition, wherein the bis(halophthalimide) composition comprises, based on the weight of the bis(halophthalimide) composition, from more than 45 to less than 75 weight percent of a 3,3'-bis(halophthalimide) of the formula

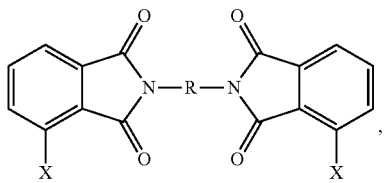

less than 10 weight percent of a 4,3'-bis(halophthalimide) of the formula

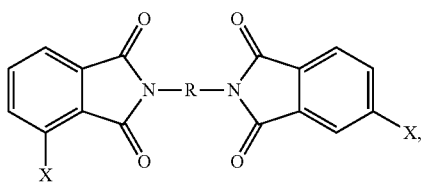

and from more than 45 to less than 75 weight percent of a (4,4'-bis(halophthalimide) of the formula

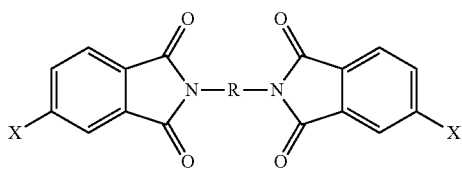

wherein each R is selected from an aromatic hydrocarbon group having 6 to 30 carbon atoms, a halogenated derivative thereof, a straight or branched chain alkylene group having 2 to 10 carbon atoms, a cycloalkylene group having 3 to 20 carbon atoms, or a divalent group of the formula

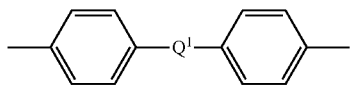

wherein $Q^1$ is selected from —O—, —S—, —C(O)—, —SO$_2$—, —SO—, —C$_y$H$_{2y}$— wherein y is 1 to 5, and a halogenated derivative thereof, to form a polyetherimide of the formula

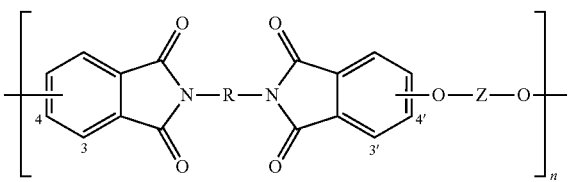

wherein n is greater than 1, each R is the same or different, each Z is the same or different, and are as defined above, and the divalent bonds between the —O—Z—O— group and the phenyl substituents are in the 3,3', 3,4', 4,3', and 4,4' positions.

7. The method of claim 6, wherein the polyetherimide has
a heat deflection temperature of at least 218° C., determined by DMA on a film sample
a heat deflection temperature at least 10° C. higher than a heat deflection temperature of the same polyetherimide manufactured using a bis(halophthalimide) composition comprising more than 10 weight percent of 3,4'-bis(halophthalimide), each determined DMA on a film sample,
at least 20% lower stiffness than the stiffness of the same polyetherimide manufactured using the bis(halophthalimide) composition comprising more than 10 weight percent of 3,4'-bis(halophthalimide), each determined by DMA over 30° C. to 110° C., on a film sample, and
a ratio of a low shear rate viscosity to a high shear rate viscosity that is at least 30% higher than the same ratio of the same polyetherimide manufactured using the bis (halophthalimide) composition comprising more than 10 weight percent of 3,4'-bis(halophthalimide) and more than 55 weight percent of the 4,4'-bis(halophthalimide), each determined by parallel plate rheometry.

8. The method of claim 6, wherein the polyetherimide comprises less than 3000 parts per million of a halide, based on the total parts of the polyetherimide.

9. The method of claim 6, wherein the polyetherimide comprises less than 5 weight percent of a cyclic byproduct, based on the total weight of the polyetherimide.

10. The method of claim 6, wherein the bis(halophthalimide) composition comprises
from 45 to less than 55 weight percent of the (3,3'-bis (halophthalimide),
less than 10 weight percent of the 3,4'-bis(halophthalimide), and
from 45 to 55 weight percent of the 4,4'-bis(halophthalimide).

11. The method of claim 6, wherein
M is sodium,
Z is a divalent radical of the formula

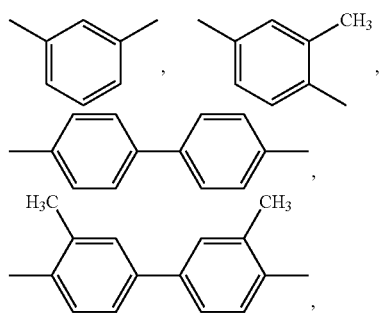

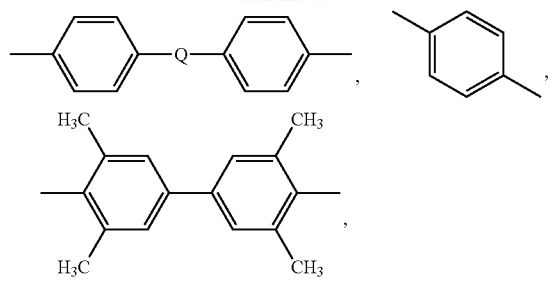

, 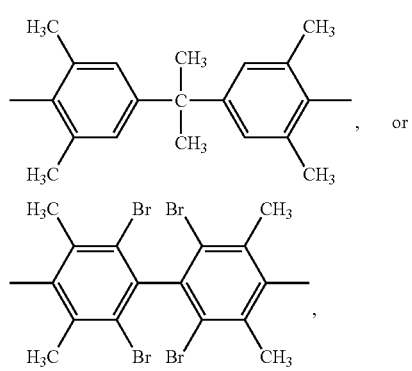, or wherein Q is selected from —O—, —S—, —C(O)—, —SO$_2$—, —SO—, —C$_y$H$_{2y}$— wherein y is an integer from 1 to 5, and a halogenated derivative thereof; and R is a divalent group of formula

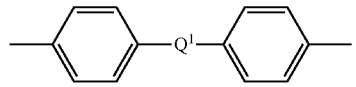

wherein Q$^1$ is —O—, —S—, —C(O)—, —SO$_2$—, —SO—, or —C$_y$H$_{2y}$— wherein y is an integer from 1 to 5.

12. The method of claim 11, wherein Z is 2,2-(4-phenylene)isopropylidene and R is m-phenylene, p-phenylene, p-phenylene diarylsulfone, or a combination thereof.

13. A method for the manufacture of a polyetherimide composition, the method comprising:

forming a bis(halophthalimide) composition according to the method of claim 2; and reacting, in the presence of a catalytically active amount of a phase transfer catalyst, an alkali metal salt of a dihydroxy aromatic compound of the formula

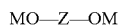
MO—Z—OM wherein M is an alkali metal salt and Z is an aromatic C$_{6-24}$ monocyclic or polycyclic moiety optionally substituted with 1 to 6 C$_{1-8}$ alkyl groups, 1 to 8 halogen atoms, or a combination thereof, with the bis(chlorophthalimide) composition, wherein the bis(chlorophthalimide) composition comprises, based on the weight of the bis(chlorophthalimide) composition, from more than 45 to less than 75 weight percent of a 3,3'-bis(chlorophthalimide) of the formula

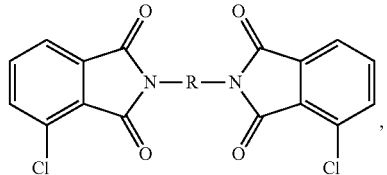

less than 10 weight percent of a 3,4'-bis(chlorophthalimide) of the formula

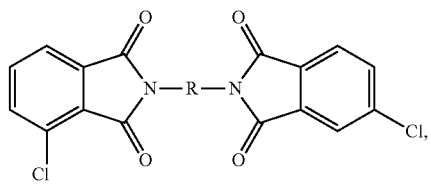

and from more than 45 to less than 75 weight percent of a (4,4'-bis(chlorophthalimide) of the formula

wherein each R is selected from an aromatic hydrocarbon group having 6 to 30 carbon atoms, a halogenated derivative thereof, a straight or branched chain alkylene group having 2 to 10 carbon atoms, a cycloalkylene group having 3 to 20 carbon atoms, or a divalent group of the formula

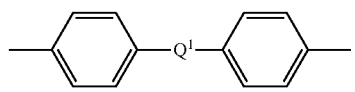

wherein Q$^1$ is selected from —O—, —S—, —C(O)—, —SO$_2$—, —SO—, and —C$_y$H$_{2y}$— wherein y is 1 to 5 and a halogenated derivative thereof, to form a polyetherimide of the formula

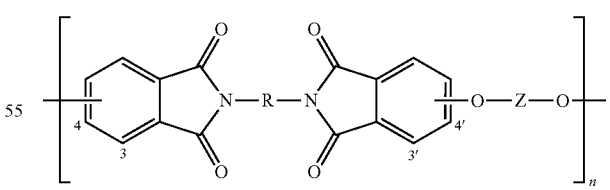

wherein n is greater than 1, each R is the same or different, each Z is the same or different, and are as defined above, and the divalent bonds between the —O—Z—O— group and the phenyl substituents are in the 3,3', 3,4', 4,3', and 4,4' positions.

14. The method of claim 13, wherein the polyetherimide has a heat deflection temperature of at least 218° C., determined by DMA on a film sample a heat deflection temperature at least 10° C. higher than the heat deflection temperature of the same polyetherimide manufactured using a bis(chlorophthalimide) composition comprising more than 10 weight percent of 3,4'-bis (chlorophthalimide), each determined by DMA on a film sample, at least 30% lower stiffness than the stiffness of the same polyetherimide manufactured using the bis(chlorophthalimide) composition comprising more than 10 weight percent of 3,4'-bis(chlorophthalimide), each determined by DMA over 30° C. to 110° C., on a film sample, and a ratio of low shear rate viscosity to high shear rate viscosity that is at least 30% higher than the same ratio of the same polyetherimide manufactured using the bis(chlorophthalimide) composition comprising more than 10 weight percent of 3,4'-bis(chlorophthalimide) and more than 55 weight percent of the 4,4'-bis(chlorophthalimide), each determined by parallel plate rheometry.

15. The composition of claim 13, wherein the polyetherimide comprises less than 3000 parts per million of chloride, based on the total parts of the polyetherimide.

16. The composition of claim 13, wherein the polyetherimide comprises less than 5 weight percent of a cyclic byproduct of the alkali metal salt and the bis(halophthalimide), based on the total weight of the polyetherimide.

17. The composition of claim 13, wherein the bis(chlorophthalimide) composition comprises
from 45 to 55 weight percent of the (3,3'-bis(chlorophthalimide),
less than 10 weight percent of the 4,3'-bis(chlorophthalimide), and
from 45 to 55 weight percent of the 4,4'-bis(chlorophthalimide).

18. The method of claim 13, wherein
M is sodium,
Z is a divalent radical of the formula

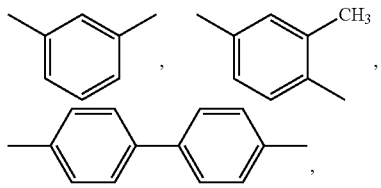

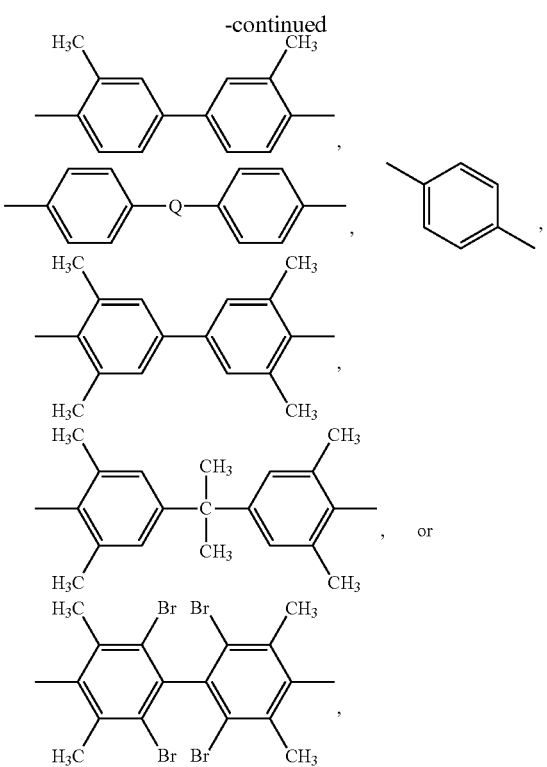

wherein Q is selected from —O—, —S—, —C(O)—, —SO$_2$—, —SO—, —C$_y$H$_{2y}$— wherein y is an integer from 1 to 5, and a halogenated derivative thereof; and
R is a divalent group of formula

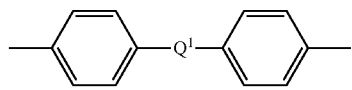

wherein Q$^1$ is —O—, —S—, —C(O)—, —SO$_2$—, —SO—, or —C$_y$H$_{2y}$— wherein y is an integer from 1 to 5.

19. The method of claim 18, wherein Z is 2,2-(4-phenylene)isopropylidene and R is m-phenylene, p-phenylene, p-phenylene diarylsulfone, or a combination thereof.

* * * * *